(12) United States Patent
Shi et al.

(10) Patent No.: US 8,816,129 B2
(45) Date of Patent: Aug. 26, 2014

(54) PTP1B INHIBITORS, SYNTHESIS THEREOF AND APPLICATION THEREOF IN PREPARATION OF MEDICAMENTS FOR TREATING TYPE 2 DIABETES MELLITUS

(75) Inventors: Dayong Shi, Shandong (CN); Shuju Guo, Shandong (CN); Xiao Fan, Shandong (CN); Weishen Lu, Shandong (CN); Yongchao Cui, Shandong (CN)

(73) Assignee: Institute of Oceanology, Chinese Academy of Sciences, Shandong (CN)

( * ) Notice: Subject to any disclaimer, the term of this patent is extended or adjusted under 35 U.S.C. 154(b) by 0 days.

(21) Appl. No.: 13/813,593

(22) PCT Filed: Jul. 7, 2011

(86) PCT No.: PCT/CN2011/076927
§ 371 (c)(1),
(2), (4) Date: Jan. 31, 2013

(87) PCT Pub. No.: WO2012/016487
PCT Pub. Date: Feb. 9, 2012

(65) Prior Publication Data
US 2013/0131182 A1  May 23, 2013

(30) Foreign Application Priority Data

Aug. 6, 2010 (CN) .......................... 2010 1 0248815

(51) Int. Cl.
*C07C 49/00* (2006.01)
*C07C 41/00* (2006.01)
*A61K 31/12* (2006.01)
*A61K 31/075* (2006.01)

(52) U.S. Cl.
USPC ........... 568/319; 568/335; 568/630; 568/631; 568/634; 568/660; 514/687; 514/721

(58) Field of Classification Search
USPC .......... 514/687, 715, 721; 568/308, 325, 332, 568/626, 631, 641
See application file for complete search history.

(56) References Cited

FOREIGN PATENT DOCUMENTS

| CN | 1853618 A | * | 1/2006 | ........... A61K 31/055 |
| CN | 1853618 A | * | 11/2006 | ........... A61K 31/055 |
| CN | 101559048 A | | 10/2009 | |
| CN | 102018688 A | | 4/2011 | |
| CN | 102018692 | * | 4/2011 | ........... A61K 31/075 |
| CN | 102018692 A | | 4/2011 | |

OTHER PUBLICATIONS

International Search Report for PCT/CN2011/076927 mailed Sep. 29, 2011 (Chinese and English language ).

* cited by examiner

*Primary Examiner* — Paul Zarek
*Assistant Examiner* — George W Kosturko
(74) *Attorney, Agent, or Firm* — Smith, Gambrell & Russell LLP

(57) ABSTRACT

The present invention relates to chemical total synthesis methods of six novel protein tyrosine phosphatase-1B (PTP1B) inhibitors and application of the inhibitors in the preparation of medicaments for treating type 2 diabetes mellitus (T2DM). The PTP1B inhibitors use one or more of the six compounds represented by the structural formulae 1, 2, 3, 4, 5 and 6, as active components. The compounds can enhance the sensitivity of an insulin receptor by inhibiting the activity of PTP1B, thereby having a favorable therapeutic effect on insulin-resistant T2DM.

10 Claims, No Drawings

PTP1B INHIBITORS, SYNTHESIS THEREOF AND APPLICATION THEREOF IN PREPARATION OF MEDICAMENTS FOR TREATING TYPE 2 DIABETES MELLITUS

FIELD OF THE INVENTION

This invention is in the field of biological medicine and specifically relates to the preparation, pharmacological activities and application of twelve bromophenol compounds, including:
(2'-bromo-6'-(dibromomethyl)-3',4'-dimethoxyphenyl)-(2,3-dibromo-4,5-dimethoxyphenyl)-methanone (1),
3,4-dibromo-5-[2'-bromo-3',4'-dihydroxy-6'-(propoxymethyl)-benzyl]-benzene-1,2-diol (2),
3,4-dibromo-5-[2'-bromo-3',4'-dihydroxy-6'-(isopropoxymethyl)-benzyl]-benzene-1,2-diol (3),
3,4-dibromo-5-[2'-bromo-6'-(butoxymethyl)-3',4'-dihydroxy-benzyl]-benzene-1,2-diol (4),
3,4-dibromo-5-[2'-bromo-3',4'-dihydroxy-6'-(isobutoxymethyl)-benzyl]--benzene-1,2-diol (5),
3,4-dibromo-5-(2-bromo-6-(sec-butoxymethyl)-3,4-dihydroxybenzyl)benzene-1,2-diol (6),
2,3-dibromo-1-[2'-bromo-6'-(2''-bromo-4'',5''-dimethoxybenzyl)-3',4'-dimethoxybenzyl]-4,5-dimethoxybenzene (7),
3,4,6-tribromo-5-(2-bromo-3,4-dihydroxy-6-(propoxyrmethyl)benzyl)benzene-1,2-diol (8),
3,4,6-tribromo-5-(2-bromo-3,4-dihydroxy-6-(isopropoxymethyl)benzyl)benzene-1,2-diol (9),
3,4,6-tribromo-5-(2-bromo-6-(butoxymethyl)-3,4-dihydroxybenzyl)benzene-1,2-diol (10),
3,4,6-tribromo-5-(2-bromo-3,4-dihydroxy-6-(isobutoxymethyl)benzyl)benzene-1,2-diol (11),
3,4,6-tribromo-5-(2-bromo-3,4-dihydroxy-6-methyl benzyl) benzene-1,2-diol (12).

All of the bromophenol derivatives are intended for treating type 2 diabetes mellitus as insulin sensitizers.

BACKGROUND OF THE INVENTION

Type 2 diabetes mellitus (T2DM) is a chronic endocrine and metabolic disorder. To date, medications for T2DM include biguanides, sulfonylureas, α-glucosidase inhibitors and thiazolidinediones. However, there are many drawbacks in their clinical use, because that the drugs are designed for symptoms not for disease target. Consequently, more efficient and safe drugs with reasonable prices are badly needed.

Insulin resistance is the key factor of T2DM. Studies demonstrated that protein tyrosine phosphatase 1B (PTP1B) has emerged as a novel therapeutic strategy for the treatments of type 2 diabetes mellitus. PTP1B plays an important role in the negative regulation of insulin signal transduction pathways. Accumulating evidences indicated that PTP1B inhibitors increased the level of phosphorylation of the insulin receptor and its substrate, and promote glucose transporter translocation and increased glucose uptake in insulin-sensitive cells. PTP1B inhibitor played insulin analogues and insulin-sensitizing agent. Knockout the PTP1B gene or inhibition of PTP1B protein and mRNA expression with antisense oligonucleotide (ASO), not only can significantly improve the insulin sensitivity of the test mice, but also significantly reduce the risk of obesity patients. Gold-stein et al, showed that the expression of PTP1B and LAR PTP in insulin target tissues of patients with insulin resistance are increased, and the increase block the activation of the insulin receptor tyrosine and insulin signal transduction. P387L Is a missense mutation of PTP1B, Echwald et al confirmed that the gene mutation frequency was 1.4% in patients with type 2 diabetes, while only 0.5% in the control group. It is speculated that the mutation in related with type 2 diabetes. Investigation of the role of PTP1B using an antisense oligonucleotide (ASO) in ob/ob mice suggest that while PTP1expression in liver, fat and skeletal muscle down, blood glucose of ob/ob mice returned to normal, and indicators of glucose metabolism also became normal. Additionally, insulin clamp experiments showed that the liver and peripheral tissues of diabetic mice enhanced insulin sensitivity. These results confirm the negative regulatory role of PTP1B in insulin signal transduction, and its increased activity may be a causative factor for insulin resistance and insulin receptor signaling impaired. Based on these data, PTP1B has already been considered as one of the best validated biological targets for T2DM.

Reported PTP1B inhibitors include: (1) Peptide PTP1B inhibitors, which contain mimetics of pTyr, have high affinity with PTP1B. But the compounds have poor chemical and biological stability. (2) Naphthnoquinone, inhibited PTP1B activity by modification of the active sites of PTPase. (3) Thiazolidinedione, improve blood glucose control by enhancing insulin sensitivities to the target organs. Representative compounds include ciglitazone, troglitazone and rosiglitazone. However, ciglitazone has been withdrawn from market due to severe hepatotoxicity. (4) Benzo[b]naphthol[2,3-d]furans and thiophenes, these compounds are designed based on benzbromarone (PTP1B inhibitor, $IC_{50}$=26 μM) and exhibited good hypoglycemic activity in mice. Unfortunately, highly negative charged, the poor cell permeability and low bioavailability of these compounds have limited their application for the development of effective drugs.

SUMMARY OF INVENTION

The invention provides twelve novel PTP1B inhibitors, which can be used for treatment of T2DM by inhibiting PTP1B and enhancing sensitivity of insulin receptor, The structures of the compounds are as follows:

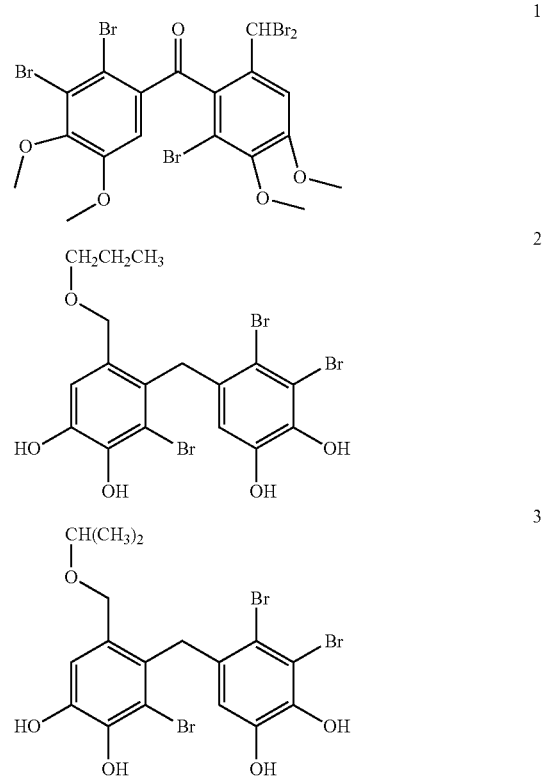

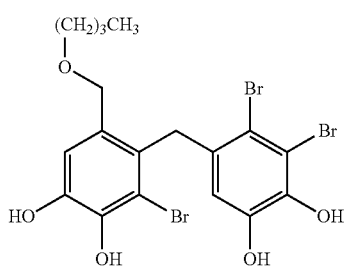

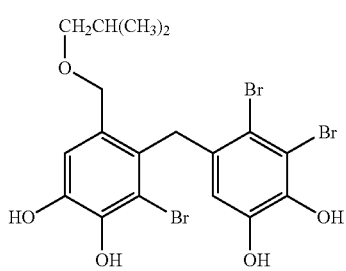

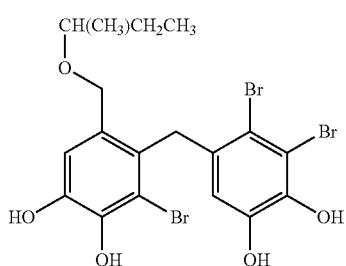

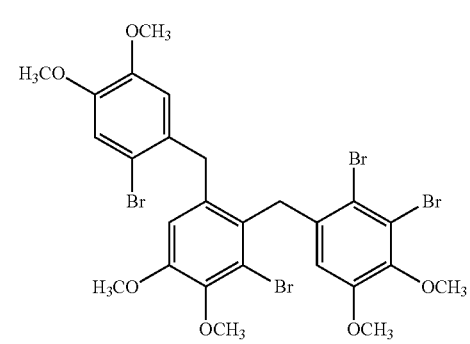

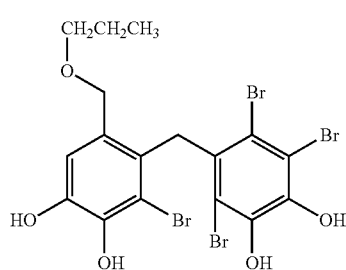

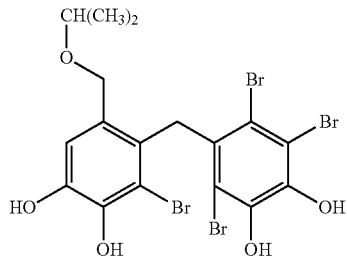

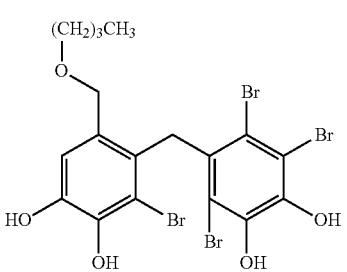

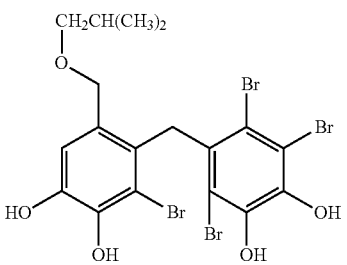

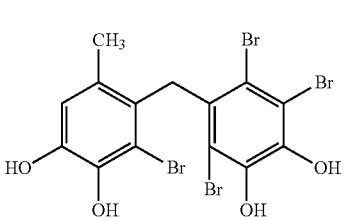

Their chemical names are:
1. (2'-bromo-6'-(dibromomethyl)-3',4'-dimethoxyphenyl)-(2,3-dibromo-4,5-dimethoxyphenyl)-methanone;
2. 3,4-dibromo-5-[2'-dibromo-3',4'-dihydroxy-6'-(propoxymethyl)-benzyl]-benzene-1,2-diol;
3. 3,4-dibromo-5-[2'-bromo-3',4'-dihydroxy-6'-(isopropoxymethyl)-benzyl]-benzene-1,2-diol;
4. 3,4-dibromo-5-[2'-bromo-6'-(butoxymethyl)-3',4'-dihydroxy-benzyl]-benzene-1,2-diol;
5. 3,4-dibromo-5-[2'-bromo-3',4'-dihydroxy-6'-(isobutoxymethyl)-benzyl]-benzene-1,2-diol;
6. 3,4-dibromo-5-[2'-bromo-3',4'-dihydroxy-6'-(secbutoxymethyl)-benzyl]-benene-1,2-diol
7. 2,3-dibromo-1-[2'-bromo-6'-(2"-bromo-4",5"-dimethoxybenzyl)-3',4'-dimethoxybenzyl]-4,5-dimethoxybenzene;
8. 3,4,6-tribromo-5-(2-bromo-3,4-dihydroxy-6-(propoxymethyl)benzyl)benzene-1,2-diol;
9. 3,4,6-tribromo-5-(2-bromo-3,4-dihydroxy-6-(isopropoxymethyl)benzyl)benzene-1,2-diol;
10. 3,4,6-tribromo-5-(2-bromo-6-(butoxymethyl)-3,4-dihydroxybenzyl)benzene-1,2-diol;
11. 3,4,6-tribromo-5-(2-bromo-3,4-dihydroxy-6-(isobutoxymethyl)benzyl)benzene-1,2-diol and
12. 3,4,6-tribromo-5-(2-bromo-3,4-dihydroxy-6-methylbenzyl)benzene-1,2-diol.

DETAILED DESCRIPTIONS OF THE INVENTION

Scheme 1 shows the preparation of (2'-bromo-6'-(dibromomethyl)-3',4'-dimethoxyphenyl)-(2,3-dibromo-4,5-dimethoxyphenyl)-methanone (1).

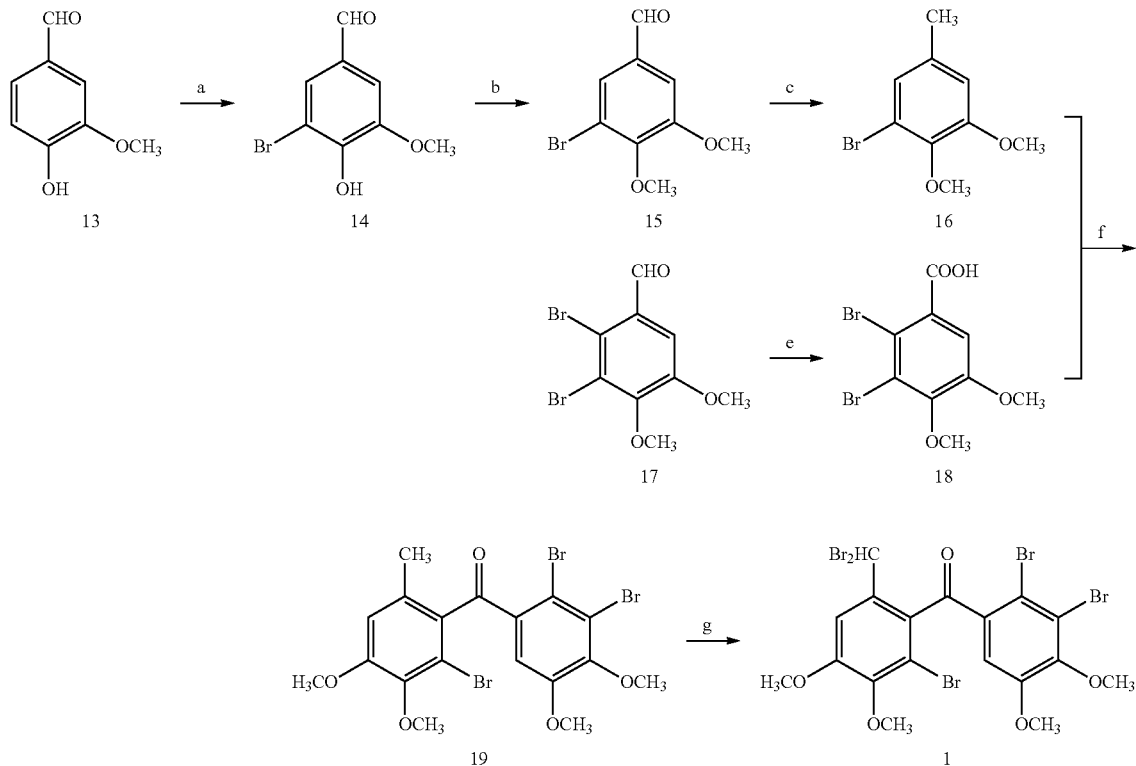

Scheme 1 (a) bromine and compound 13 (molar ratio is 1:1), MeOH, ice bath condition; (b) Methyl iodide and compound 14 (molar ratio is 1:1~1:1.5), $K_2CO_3$, DMF as solvent, room temperature; (c) a solution of compound 15 in diglycol (mass concentration of compound 15; 10~15%), mass concentration 80% hydrazine hydrate solution, KOH, 110~120° C.; (d) bromine and compound 15 (molar ratio is 2:1~3:1), acetic acid, 60~70° C.; (e) $KMnO_4$, water, 90° C.; (f) Trifluoroacetic anhydride, $H_3PO_4$, 0~60° C.; (a) N-Bromosuccinimide, AIBN, $CCl_4$, hv.

Synthesis and Characterization of 5-bromo-vanilline (14)

Under ice bath condition, to a solution of vanilline in MeOH (mass ratio, vanilline:MeOH=1:6~1:7) was added dropwise bromine (mole ratio, vanilline:bromine=1:1) within 1-2 hours. The mixture was warmed to room temperature and stirred for further 0.5-1 hour. The mixture was cooled to 0° C. and added ice water (volume ratio, $H_2O$:MeOH=1:2~1:3) within 20-30 min, then precipitate was separated out. The mixture was stirred for further 15-30 min. The precipitate was filtered and washed with ice water and dried to give white solid. Spectrum analysis verified the compound is 5-Br-vanillin.

The physical and chemical properties of 5-Br-vanillin: m.p. 160-162° C. $^1$H-NMR (500 MHz, $CDCl_3$) δ: 9.78 (s, 1H), 7.64 (d, J=1.65 Hz, 1H), 7.36 (d, J=1.65 Hz, 2H), 3.98 (s, 3H); $^{13}$C-NMR (125 MHz, $CDCl_3$) δ: 189.5 (CHO), 148.9 (C), 147.7 (C), 130.1, 130.0 (C), 108.2 (C), 108.1 (CH), 56.6 ($CH_3$).

Synthesis and Characterization of 5-bromo-veratraldehyde (15)

To a suspension of 5-Br-vanillin and $K_2CO_3$ in DMF (mass ratio, $K_2CO_3$:DMF=1:8~1:12) was added dropwise $CH_3I$ (mole ratio, 5-Br-vanillin:$CH_3I$=1:1~1:1.5) at room temperature. After stirring for 24 h, brine (18-22%) was added to quench the reaction. The mixture was extracted with tert-butyl methyl ether three times. The organic layer was collected, washed with brine (18-22%), dried over anhydrous $Na_2SO_4$ and concentrated in vacuo to give white solid. Spectrum analysis verified the compound is 5-bromo-veratraldehyde.

The physical and chemical properties: m.p. 60-62° C., $^1$H--NMR (500 MHz, $CDCl_3$) δ: 9.84 (s, 1H), 7.64 (s, 1H), 7.38 (s, 1H), 3.94 (s, 3H), 3.93 (s, 3H); $^{13}$C-NMR (125 MHz, $CDCl_3$) δ: 189.7 (CHO), 154.2 (C), 151.8 (C), 133.1 (C), 128.7 (CH), 117.9 (CH), 110.2 (C), 60.8 ($CH_3$), 56.2 ($CH_3$).

Synthesis and Characterization of 5-bromo-3,4-dimethoxy-methylbenzene (16)

To a solution of 5-bromo-veratraldehyde in diglycol was added 80% hydrazine hydrate (mole ratio, 3-bromo-4,5-dimethoxybenzaldehyde:hydrazine hydrate=1:1~1:1.5) at room temperature. TLC was used to monitor the reaction. Then KOH (8-12%) was added. The mixture was heated to 110-120° C. and stirred for 2-3 hours. After cooling, the resulting mixture was poured into water, and extracted with $CH_2Cl_2$ for three times. The organic layer was collected, washed with 1 mol/L HCl, dried over anhydrous $MgSO_4$ and concentrated in vacuo to give colorless oil. Spectrum analysis verified the compound is 5-bromo-3,4-dimethoxy-methylbenzene.

The physical and chemical properties: $^1$H-NMR (500 MHz, $CDCl_3$) δ: 6.94 (s, 1H), 6.65 (s, H), 3.84 (s, 3H), 3.82 (s, 3H), 2.28 (s, 3H); $^{13}$C-NMR (125 MHz, $CDCl_3$) δ: 153.3 (C), 144.1 (C), 135.1 (C), 124.8 (CH), 117.1 (C), 112.5 (CH), 60.4 (CH$_3$), 55.9 (CH$_3$), 21.0 (CH$_3$).

Synthesis and Characterization of 5,6-dibromo-veratraldehyde (17)

At room temperature, to a solution of 3-bromo-4,5-dimethoxybenzaldehyde in AcOH (mass concentration: 10-15%) was added dropwise bromine (mole ratio, bromine: 3-bromo-4,5-dimethoxybenzaldehyde=2:1~3:1) and catalyst iron powder. The mixture was heated at 60-70° C. and stirred for 4-6 hours. After cooling to room temperature, the iron powder was filtered and the filtrate was removed in vacuo. The residue was redissolved in CHCl$_3$, and washed with 5% Na$_2$SO$_3$ for two times. The organic layer was collected, and concentrated in vacuo. The residue was recrystallized in acetone to give white needle crystal. Spectrum analysis verified the compound is 5,6-dibromo-veratraldehyde.

The physical and chemical properties: m.p. 128-130° C. $^1$H-NMR (500 MHz, CDCl$_3$) δ: 10.27 (s, 1H), 7.48 (s, 1H), 3.94 (s, 3H), 3.92 (s, 3H); $^{13}$C-NMR (125 MHz, CDCl$_3$) δ: 191.5 (CHO), 152.8 (C), 131.0 (C), 122.8 (C), 121.9 (C), 111.7 (CH), 60.8 (CH$_3$), 56.3 (CH$_3$).

Synthesis and Characterization of 5,6-dibromo-veratric acid (18)

NaHCO$_3$, 5,6-dibromo-veratraldehyde and H$_2$O were successively placed in a three-necked round bottom flask. The suspension was heated to 90° C. and added KMnO$_4$ (mole ratio, KMnO$_4$:2,3-dibromo-4,5-dimethoxybenzaldehyde=1: 1~1:1.5) in three portions. TLC was used to monitor the reaction. The MnO$_2$ was filtered and the filtrate was acidified. The white precipitate was filtered and dried to give white solid. Spectrum analysis verified the compound is 5,6-dibromo-veratric acid.

The physical and chemical properties: m.p. 180-181° C.; $^1$H NMR (500 MHz, CD$_3$OCD$_3$): δ 7.39 (s, 1H, H-2), 3.90 (s, 3H, H-8), 3.87 (s, 3H, H-9); $^{13}$C NMR (125 MHz, CD$_3$OCD$_3$): δ 169.2 (C-7), 153.6 (C-4), 150.9 (C-3), 132.8 (C-1), 127.5 (C-6), 123.8 (C-5), 114.5 (C-2), 60.9 (C-8), 56.9 (C-9).

Synthesis and Characterization of (2-bromo-3,4-dimethoxy-6-methylphenyl)-(2,3-dibromo-4,5-dimethoxyphenyl)-methanone (19)

Under ice bath condition, 5,6-dibromo-veratric acid was placed in a three-necked round bottom flask and dissolved in TFAA. To the stirred solution was added 85% H$_3$PO$_4$ and 1-bromo-2,3-dimethoxy-5-methylbenzene (mole ratio, 2,3-dibromo-4,5-dimethoxybenzoic acid :1-bromo-2,3-dimethoxy-5-methylbenzene=1:1). The mixture was heated to 60° C. and TLC was used to monitor the reaction. The mixture was poured into crushed ice and extracted with CHCl$_3$ for three times. The organic layer was collected and concentrated in vacuo. The residue was recrystallized in EtOH to give white crystal. Spectrum analysis verified the compound is (2-bromo-3,4-dimethoxy-6-methylphenyl)-(2, 3-dibromo-4,5-dimethoxyphenyl)-methanone.

The physical and chemical properties: m.p. 86-88° C., $^1$H NMR (500 MHz, CDCl$_3$): δ 7.16 (s, 1H, H-6), 6.74 (s, 1H, H-5'), 3.91 (s, 3H, H-9), 3.90 (s, 3H, H-11), 3.81 (s, 3H, H-10), 3.79 (s, 3H, H-12), 2.22 (s, 3H, H-8); $^{13}$C NMR (125 MHz, CDCl$_3$); δ 194.2 (C-7), 154.0 (C-4), 152.0 (C-4'), 150.8 (C-5), 144.6 (C-3'), 135.7 (C-1), 133.7 (C-1'), 133.0 (C-6'), 124.3 (C-2), 116.3 (C-2'), 115.5 (C-3), 115.1 (C-6), 113.8 (C-5'), 60.6 (C-9,11), 56.3 (C-10), 56.0 (C-12), 20.2 (C-8).

Synthesis and Characterization of (2-bromo-6-(dibromomethyl)-3,4-dimethoxyphenyl)-(2,3-dibromo-4,5-dimethoxyphenyl)-methanone (1)

(2-bromo-3,4-dimethoxy-6-methylphenyl)-(2,3-dibromo-4,5-dimethoxyphenyl)-methanone and catalyst AIBN was placed in a three-necked round bottom flask, and dissolved in CCl$_4$. Under hv condition, to the solution was added NBS with stirring. TLC was used to monitor the reaction. The precipitate was filtered off and the filtrate was removed in vacuo to produce a brownish residue. The residue was purified by chromatography to give white solid. Spectrum analysis verified the compound is (2-bromo-6-(dibromomethyl)-3, 4-dimethoxyphenyl)-(2,3-dibromo-4,5-dimethoxyphenyl)-methanone.

The physical and chemical properties: m.p. 166-169° C.; $^1$H NMR (500 MHz, CDCl$_3$): δ 7.58 (s, 1 H), 7.07 (s, 1H), 6.66 (s, 1H), 4.03 (s, 3H), 3.93 (s, 3H), 3.87 (s, 3H), 3.78 (s, 3H); $^{13}$C NMR (125 MHz, CDCl$_3$): δ 192.8 (CO), 155.1, 152.0, 151.2, 147.6, 137.4, 135.2, 129.2, 124.7, 116.8, 115.1, 114.4, 113.5, 60.8 (2×CH$_3$), 56.4 (2×CH$_3$), 36.7 (CHBr$_2$); HRMS: [M+H]$^+$ calcd for C$_{18}$H$_{16}$O$_5$Br$_5$: 706.6915, found: 706.6882.

Scheme 2 shows the preparation of
3,4-dibromo-5-[2'-bromo-3',4'-dihydroxy-6'-(propoxymethyl)-benzyl]-benzene-1,2-diol (2),
3,4-dibromo-5-[2'-bromo-3',4'-dihydroxy-6'-(isopropoxymethyl)-benzyl]-benzene-1,2-diol (3),
3,4-dibromo-5-[2'-bromo-6'-(butoxymethyl)-3',4'-dihydroxy-benzyl]-benzene-1,2-diol (4),
3,4-dibromo-5-[2'-bromo-3',4'-dihydroxy-6'-(isobutoxymethyl)-benzyl]-benzene-1,2-diol (5) and
3,4-dibromo-5-(2-bromo-6-(sec-butoxymethyl)-3,4-dihydroxybenzyl)benzene-1,2-diol (6)

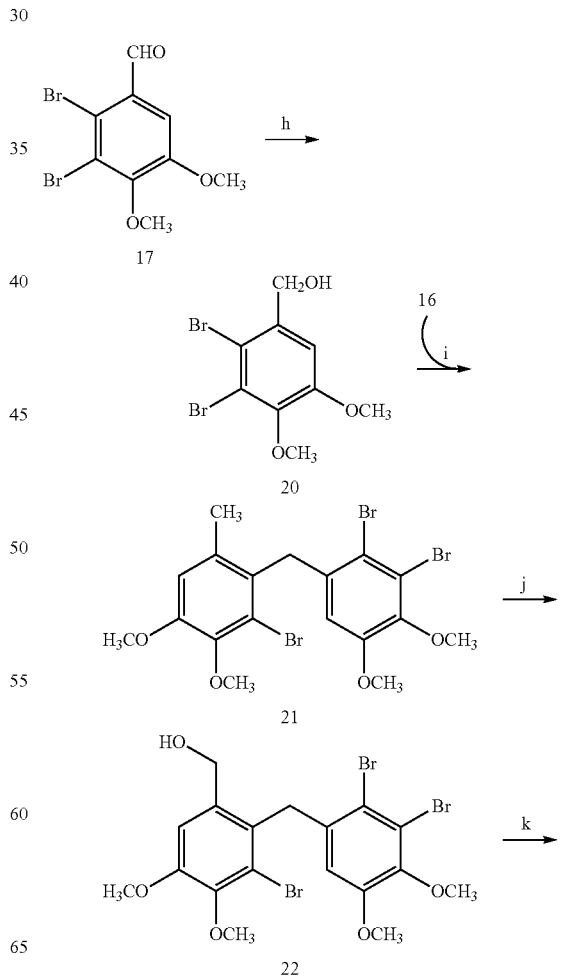

-continued

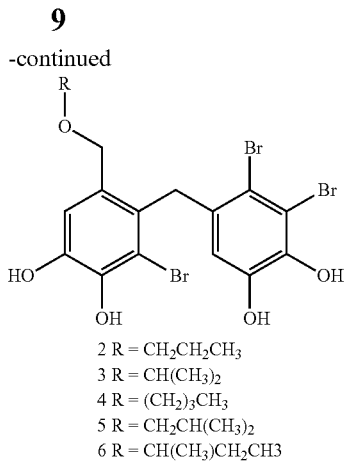

2 R = CH₂CH₂CH₃
3 R = CH(CH₃)₂
4 R = (CH₂)₃CH₃
5 R = CH₂CH(CH₃)₂
6 R = CH(CH₃)CH₂CH3

Scheme 2 (h) NaBH$_4$, MeOH, 0° C.; (i) AlCl$_3$, CH$_2$Cl$_2$, 0° C.; (j) N-Bromosuccinimide, CCl$_4$, hv; H$_2$O, dioxane, reflux; (k) BBr$_3$, CH$_2$Cl$_2$, 0° C.; H$_3$PO$_4$, corresponding alcohol, 70~80° C.

Synthesis and Characterization of 5,6-dibromo-3,4-dimethoxy-phenyl-methanol (20)

Under ice bath condition, to a stirred solution of 5,6-dibromo-veratraldehyde in MeOH (with mass concentration 15-20%) was added NaBH$_4$ (mole ratio, NaBH$_4$:5,6-dibromo-veratraldehyde=1:4~1:3). TLC was used to monitor the reaction. 10% HCl was added into the reaction to acidified pH=5-6. MeOH was evaporated and the residue was extracted with CH$_2$Cl$_2$. The organic layer was collected, dried over anhydrous MgSO$_4$ and concentrated in vacuo to give white solid. Spectrum analysis verified the compound is 5,6-dibromo-3,4-dimethoxy-phenyl-methanol.

The physical and chemical properties: m.p. 91~93° C. $^1$H-NMR (500 MHz, CDCl$_3$) δ: 7.01 (s, 1H), 4.71 (s, 2H), 3.88 (s, 3H), 3.84 (s, 3H); $^{13}$C-NMR (125 MHz, CDCl$_3$) δ: 152.7 (C), 146.8 (C), 137.3 (C), 121.7 (C), 114.9 (C), 111.5 (CH), 65.9 (CH$_2$), 60.5 (CH$_3$), 56.2 (CH$_3$).

Synthesis and Characterization of 2,3-dibromo-1-(2'-bromo-3',4'-dimethoxy-6'-methylbenzyl)-4,5-dimethoxy benzene (21)

Under ice bath condition, to a stirred solution of 5-bromo-3,4-dimethoxy-methylbenzene and 5,6-dibromo-3,4-dimethoxy-phenyl-methanol in CH$_2$Cl$_2$ (with mass concentration 4-10%) was added AlCl$_3$ (mole ratio, AlCl$_3$:1-bromo-2,3-dimethoxy-5-methylbenzene:2,3-dibromo-4,5-dimethoxy-phenyl-methanol=1:1:1) in three portions. TLC was used to monitor the reaction. The mixture was poured into ice water. The organic layer was washed with 3% HCl three times, dried over anhydrous MgSO$_4$ and concentrated in vacuo. The residue was recrystallized from MeOH to give white solid. Spectrum analysis verified the compound is 2,3-dibromo-1-(2'-bromo-3',4'-dimethoxy-6'-methylbenzyl)-4,5-dimethoxy benzene The physical and chemical properties: m.p. 114-117° C. $^1$H-NMR (500 MHz, CDCl$_3$) δ: 6.76 (s, 1H), 6.15 (s, 1H), 4.19 (s, 2H), 3.89 (s, 3H), 3.84 (s, 3H), 3.81 (s, 3H), 3.56 (s, 3H), 2.17 (s, 3H); $^{13}$C-NMR (125 MHz, CDCl$_3$) δ: 152.5 (C), 152.0 (C), 146.1 (C), 144.9 (C), 135.8 (C), 134.3 (C), 129.6 (C), 122.1 (C), 121.7 (C), 117.6 (CH), 113.8 (CH), 111.7 (CH), 60.4 (2×CH$_3$), 56.1 (CH$_3$), 56.0 (CH$_3$), 40.5 (CH$_2$), 20.6 (CH$_3$).

Synthesis and Characterization of (3-bromo-2-(2',3'-dibromo-4',5'-dimethoxybenzyl)-4,5-dimethoxyphenyl)-methanol (22)

Under hv condition, to a solution of catalyst AIBN or BPO and 2,3-dibromo-1-(2'-bromo-3',4'-dimethoxy-6'-methylbenzyl)-4,5-dimethoxy benzene and in CCl$_4$ (mass concentration 5~10%) was added NBS (mole ratio, AIBN or BPO:2,3-dibromo-1-(2'-bromo-3',4'-dimethoxy-6'-methylbenzyl)-4,5-dimethoxy benzene=1:100, NBS:2,3-dibromo-1-(2'-bromo-3',4'-dimethoxy-6'-methylbenzyl)-4,5-dimethoxy benzene=1.1:1) with stirring. TLC was used to monitor the reaction. Then hv stopped. The precipitate was filtered off and the solvent was removed in vacuo to produce a brownish residue. The residue was purified by chromatography eluted with petroleum ether and ethyl acetate (8:1) to give white solid. The white solid (mass concentration 5~10%) and K$_2$CO$_3$ (mass concentration 5~10%) were dissolved in mixture of dixoane and H$_2$O (volume ratio, 1:1) and the reaction was heated to 90-100° C. TLC was used to monitor the reaction. The mixture was extracted with CHCl$_3$. The organic layer was collected and concentrated in vacuo to give white solid. Spectrum analysis verified the compound is (3-bromo-2-(2',3'-dibromo-4',5'-dimethoxybenzyl)-4,5-dimethoxyphenyl)-methanol.

The physical and chemical properties: m.p. 164-166° C. $^1$H-NMR (500 MHz, CDCl$_3$) δ: 7.09 (s, 1 H), 6.14 (s, 1H), 4.52 (s, 2H), 4.22 (s, 2H), 3.91 (s, 3H), 3.86 (s, 3H), 3.79 (s, 3H), 3.55 (s, 3H); $^{13}$C-NMR (125 MHz, CDCl$_3$) δ: 152.4 (2×C), 146.1 (C), 145.9 (C), 136.6 (C), 135.8 (C), 128.7 (C), 122.5 (C), 121.7 (C), 117.4 (C), 111.8 (CH), 111.4 (CH), 63.0 (CH$_2$), 60.4 (2×CH$_3$), 56.0 (2×CH$_3$), 39.2 (CH$_2$).

Synthesis and Characterization of 3,4-dibromo-5-(2-bromo-3,4-dihydroxy-6-(propoxymethyl)benzyl)benzene-1,2-diol (2)

Under 0° C. condition, to a solution of 3-bromo-2-(2',3'-dibromo-4',5'-dimethoxybenzyl)-4,5-dimethoxyphenyl)-methanol in CH$_2$Cl$_2$ was added dropwise 1 mol·L$^{-1}$ BBr$_3$ dichloromethane solution. Molar ratio of BBr$_3$ and (3-bromo-2-(2',3'-dibromo-4',5'-dimethoxybenzyl)-4,5-dimethoxyphenyl)-methanol was 6:1~8:1. The reaction mixture stirred over night at room temperature. Then the mixture was poured into ice-cold water and extracted with ethyl acetate for three times. The organic layer was collected, and concentrated in vacuo. The residue was dissolved in n-propanol. Then 1-5 mL 85% H$_3$PO$_4$ was added. After refluxing for 10-12 hours, the n-propanol was removed in vacuo. The residue was purified by column chromatography eluted with petroleum ether:ethyl acetate=1:1 to produce yellow solid. Spectrum analysis verified the compound is 3,4-dibromo-5-(2-bromo-3,4-dihydroxy-6-(propoxymethyl)benzyl)benzene-1,2-diol. The physical and chemical properties: $^1$H NMR (500 MHz, DMSO-d$_6$): δ 9.75 (s, 1H), 9.69 (s, 1H), 9.27 (s, 1H), 9.14 (s, 1H), 6.88 (s, 1H), 6.05 (s, 1H), 4.17 (s, 2H), 3.99 (s, 2H), 3.26 (t, 6.52, 2H), 1.14 (m, J=, 2H), 0.79 (t, J=7.36, 3H); 13C NMR (125 MHz, DMSO-d$_6$): δ 144.9 (C), 144.3 (C), 142.5 (2×C), 130.5 (C), 129.0 (C), 127.5 (C), 115.4, 114.6 (C), 114.3, 113.9 (C), 112.9 (C), 71.2 (CH$_2$), 70.3 (CH$_2$), 38.3 (CH$_2$), 22.2 (CH$_2$), 10.4 (CH$_3$); EIMS m/z 544/542/540/538[M]$^+$ (1/3/3/1), 484/482/480/478 (2/7/7/2), 467/465/463/461 (2/6/6/2), 403/401/399 (7/15/7), 322/320 (19/18), 82/80 (42/43), 59 (100); HRMS: [M—H]$^−$ calcd for C$_{17}$H$_{16}$O$_5$$^{79}$Br$_3$: 536.8548; found: 536.8570.

Synthesis and Characterization of 3,4-dibromo-5-(2-bromo-3,4-dihydroxy-6-(isopropoxymethyl)benzyl)benzene-1,2-diol (3)

Under 0° C. condition, to a solution of 3-bromo-2-(2',3'-dibromo-4',5'-dimethoxybenzyl)-4,5-dimethoxyphenyl-methanol in CH$_2$Cl$_2$ (with mass concentration 5~10%) was added dropwise 1 mol·L$^{-1}$ BBr$_3$ dichloromethane solution. Molar ratio of BBr$_3$ and (3-bromo-2-(2',3'-dibromo-4',5'-dimethoxybenzyl)-4,5-dimethoxyphenyl)-methanol was 6:1~8:1. The reaction mixture stirred over night at room temperature. Then the mixture was poured into ice-cold water and extracted with ethyl acetate for three times. The organic layer was collected, and concentrated in vacuo. The residue was dissolved in iso-propanol. Then 1-5 mL 85% H$_3$PO$_4$ was added. After refluxing for 10-12 hours, the iso-propanol was removed in vacuo. The residue was purified by column chromatography eluted with petroleum ether:ethyl acetate=1:1 to produce yellow solid. Spectrum analysis verified the compound is 3,4-dibromo-5-(2-bromo-3,4-dihydroxy-6-(isopropoxymethyl)benzyl)benzene-1,2-diol.

The physical and chemical properties: $^1$H NMR (500 MHz, DMSO-d$_6$): δ 9.72 (s, 1H), 9.69 (s, 1H), 9.26 (s, 1H), 9.11 (s, 1H), 6.88 (s, 1H), 6.05 (s, 1H), 4.15 (s, 2H), 3.98 (s, 2H), 3.51 (m, J=6.43, 2H), 1.02 (d, J=6.43, 6H); $^{13}$C NMR (125 MHz, DMSO-d$_6$): δ 144.9 (C), 144.3 (C), 142.5 (C), 142.4 (C), 130.5 (C), 129.3 (C), 127.5 (C), 115.4 (CH), 114.5 (C), 114.3 (C), 113.9 (CH), 112.9 (C), 79.1 (CH), 67.6 (CH$_2$), 38.3 (CH$_2$), 21.7 (2×CH$_3$); EIMS m/z 544/542/540/538[M]$^+$ (1/3/3/1), 484/482/480/478 (2/7/7/2), 467/465/463/461 (2/6/6/2), 403/401/399 (5/10/5), 322/320 (10/9), 82/80 (98/100), 59 (30); HRMS: [M—H]$^-$ calcd for C$_{17}$H$_{16}$O$_5$$^{79}$Br$_3$: 536.8548; found: 536.8525.

Synthesis and Characterization of 3,4-dibromo-5-(2-bromo-6-(butoxymethyl)-3,4-dihydroxybenzyl)benzene-1,2-diol (4)

Under 0° C. condition, to a solution of 3-bromo-2-(2',3'-dibromo-4',5'-dimethoxybenzyl)-4,5-dimethoxyphenyl-methanol in CH$_2$Cl$_2$ (with mass concentration 5~10%) was added dropwise 1 mol·L$^{-1}$ BBr$_3$ dichloromethane solution. Molar ratio of BBr$_3$ and (3-bromo-2-(2',3'-dibromo-4',5'-dimethoxybenzyl)-4,5-dimethoxyphenyl)-methanol was 6:1~8:1. The reaction mixture stirred over night at room temperature. Then the mixture was poured into ice-cold water and extracted with ethyl acetate for three times. The organic layer was collected, and concentrated in vacuo. The residue was dissolved in n-butyl alcohol. Then 1-5 mL 85% H$_3$PO$_4$ was added. After refluxing for 10-12 hours, the n-butyl alcohol was removed in vacuo. The residue was purified by column chromatography eluted with petroleum ether:ethyl acetate=1:1 to produce yellow solid. Spectrum analysis verified the compound is 3,4-dibromo-5-(2-bromo-6-(butoxymethyl)-3,4-dihydroxybenzyl)benzene-1,2-diol.

The physical and chemical properties: $^1$H NMR (500 MHz, DMSO-d$_6$): δ 9.75 (s, 1H), 9.69 (s, 1H), 9.27 (s, 1H), 9.15 (s, 1H), 6.87 (s, 1H), 6.04 (s, 1H), 4.16 (s, 2H), 3.98 (s, 2H), 3.29 (t, J=6.44, 2H), 1.36 (m, 2H), 1.22 (m, 2H), 0.80 (t, J=7.35, 3H); $^{13}$C NMR (125 MHz, DMSO-d$_6$): δ 144.9 (C), 144.2 (C), 142.5 (2×C), 130.5 (C), 129.0 (C), 127.5 (C), 115.4 (CH), 114.6 (C), 114.3 (CH), 113.9 (C), 112.9 (C), 70.4 (CH$_2$), 69.2 (CH$_2$), 38.3 (CH$_2$), 31.1 (CH$_2$), 18.7 (CH$_2$), 13.6 (CH$_3$); EIMS m/z 484/482/480/478 (2/7/7/2), 467/465/463/461 (2/6/6/2), 403/401/399 (5/10/5), 322/320 (13/12), 82/80 (18/18), 59 (100); HRMS: [M—H]$^-$ calcd for C$_{18}$H$_{18}$O$_5$$^{79}$Br$_3$: 550.8704; found: 550.8688.

Synthesis and Characterization of 3,4-dibromo-5-(2-bromo-3,4-dihydroxy-6-(isobutoxymethyl)benzyl)benzene-1,2-diol (5)

Under 0° C. condition, to a solution of 3-bromo-2-(2',3'-dibromo-4',5'-dimethoxybenzyl)-4,5-dimethoxyphenyl-methanol in CH$_2$Cl$_2$ (with mass concentration 5~10%) was added dropwise 1 mol·L$^{-1}$ BBr$_3$ dichloromethane solution. Molar ratio of BBr$_3$ and (3-bromo-2-(2',3'-dibromo-4',5'-dimethoxybenzyl)-4,5-dimethoxyphenyl)-methanol was 6:1~8:1. The reaction mixture stirred over night at room temperature. Then the mixture was poured into ice-cold water and extracted with ethyl acetate for three times. The organic layer was collected, and concentrated in vacuo. The residue was dissolved in isobutanol. Then 1-5 mL 85% H$_3$PO$_4$ was added. After refluxing for 10-12 hours, the isobutanol was removed in vacuo. The residue was purified by column chromatography eluted with petroleum ether:ethyl acetate=1:1 to produce yellow solid. Spectrum analysis verified the compound is 3,4-dibromo-5-(2-bromo-3,4-dihydroxy-6-(isobutoxymethyl)benzyl)benzene-1,2-diol.

The physical and chemical properties: $^1$H NMR (500 MHz, DMSO-d$_6$): δ 9.75 (s, 1H), 9.69 (s, 1H), 9.27 (s, 1H), 9.15 (s, 1H), 6.88 (s, 1H), 6.04 (s, 1H), 4.16 (s, 2H), 3.98 (s, 2H), 3.08 (d, J=6.48, 2H), 1.68 (m, 1H), 0.78 (d, J=6.68, 6H); $^{13}$C NMR (125 MHz, DMSO-d$_6$): δ 144.9 (C), 144.2 (C), 142.5 (2×C), 130.5 (C), 129.0 (C), 127.5 (C), 115.4 (CH), 114.6 (C), 114.3 (CH), 113.9 (C), 113.0 (C), 76.4 (CH$_2$), 70.6 (CH$_2$), 38.3 (CH$_2$), 27.8 (CH), 19.1 (2×CH$_3$); EIMS m/z 558/556/554/552 [M]$^+$ (1/3/3/1), 484/482/480/478 (5/15/14/5), 467/465/463/461 (3/9/10/3), 404/402/400 (5/10/7), 403/401/399 (10/21/10), 322/320 (27/25), 82/80 (99/100), 57 (40); HRMS: [M—H]$^-$ calcd for C$_{18}$H$_{18}$O$_5$$^{79}$Br$_3$: 550.8704; found: 550.8688.

Synthesis and Characterization of 3,4-dibromo-5-(2-bromo-6-(sec-butoxymethyl)-3,4-dihydroxybenzyl)benzene-1,2-diol (6)

Under 0° C. condition, to a solution of 3-bromo-2-(2',3'-dibromo-4',5'-dimethoxybenzyl)-4,5-dimethoxyphenyl-methanol in CH$_2$Cl$_2$ (with mass concentration 5~10%) was added dropwise 1 mol·L$^{-1}$ BBr$_3$ dichloromethane solution. Molar ratio of BBr$_3$ and (3-bromo-2-(2',3'-dibromo-4',5'-dimethoxybenzyl)-4,5-dimethoxyphenyl)-methanol was 6:1~8:1. The reaction mixture stirred over night at room temperature. Then the mixture was poured into ice-cold water and extracted with ethyl acetate for three times. The organic layer was collected, and concentrated in vacuo. The residue was dissolved in sec-butyl alcohol. Then 1-5 mL 85% H$_3$PO$_4$ was added. After refluxing for 10-12 hours, the sec-butyl alcohol was removed in vacuo. The residue was purified by column chromatography eluted with petroleum ether:ethyl acetate=1:1 to produce yellow solid. Spectrum analysis verified the compound is 3,4-dibromo-5-(2-bromo-6-(sec-butoxymethyl)-3,4-dihydroxybenzyl)benzene--1,2-diol.

The physical and chemical properties: $^1$H NMR (500 MHz, DMSO-d$_6$): δ 9.73 (s, 1H), 9.70 (s, 1H), 9.28 (s, 1H), 9.13 (s, 1H), 6.88 (s, 1H), 6.04 (s, 1H), 4.20 (d, J=11.36, 1H), 4.10 (d, J=11.36, 1H), 3.99 (s, 2H), 3.29 (m, 1H) 1.35 (m, 2H), 1.00 (d, J=6.11, 3H), 0.77 (t, J=7.40, 3H); $^{13}$C NMR (125 MHz, DMSO-d$_6$): δ 144.9, 144.2, 142.5, 142.4, 130.5, 129.4, 127.4, 115.5, 114.5, 114.3, 113.9, 113.0, 75.2, 67.8, 38.3, 28.4, 18.6, 9.3; HRESIMS m/z 550.8728 ([M—H]$^-$, C$_{18}$H$_{18}$O$_5$Br$_3$, calc 550.8704)

Scheme 3 shows the preparation of 2,3-dibromo-1-(2'-bromo-6'-(2"-bromo-4",5"-dimethoxybenzyl)-3',4'-dimethoxybenzyl)-4,5-dimethoxybenzene (7).

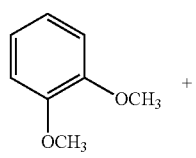

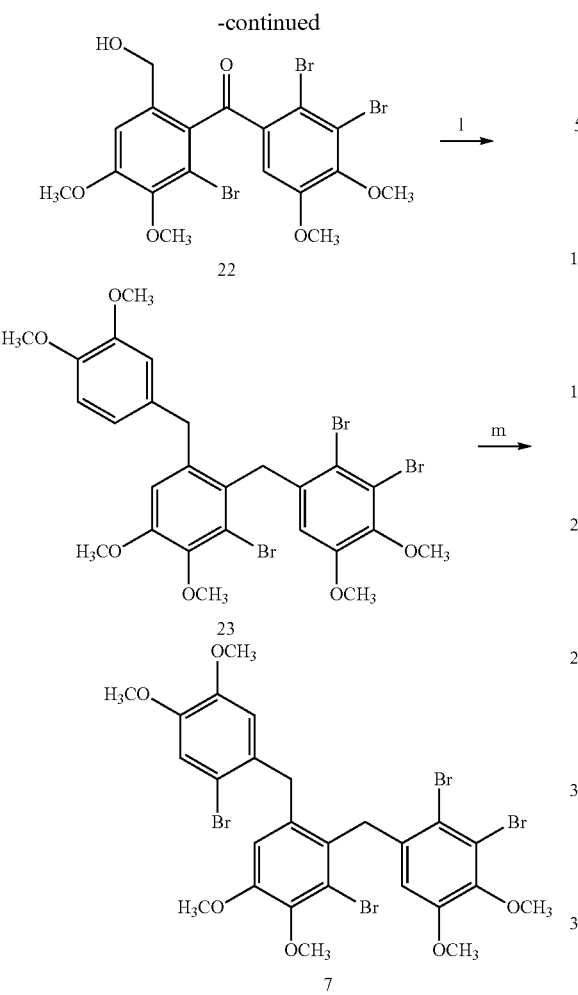

23

7

Scheme 3 (1) AlCl$_3$, CH$_2$Cl$_2$, room temperature; (m) Bromine, CH$_2$Cl$_2$.

Synthesis and Characterization of 2,3-dibromo-1-(2'-bromo-6'-(3",4"-dimethoxybenzyl)-3',4'-dimethoxybenzyl)-4,5-dimethoxybenzene (23)

Under ice bath condition, to a solution of veratrole (mass concentration 5~10%) and (3-bromo-2-(2',3'-dibromo-4',5'-dimethoxybenzyl)-4,5-dimethoxyphenyl)-methanol (mass concentration 5~10%) in CH$_2$Cl$_2$ was added AlCl$_3$ (mole ratio, AlCl$_3$:veratrole:(3-bromo-2-(2',3'-dibromo-4',5'-dimethoxybenzyl)-4,5-dimethoxyphenyl)-methanol=1.2:1:1) with stirring. TLC was used to monitor the reaction. The mixture was poured into ice-water. The organic phase was washed with 3% HCl for three times, then dried over anhydrous MgSO$_4$, and concentrated in vacuo. The residue was recrystallized from MeOH to give white solid. Spectrum analysis verified the compound is 2,3-dibromo-1-(2'-bromo-6'-(3",4"-dimethoxybenzyl)-3',4'-dimethoxybenzyl)-4,5-dimethoxybenzene.

The physical and chemical properties: m.p. 138-139' C. $^1$H-NMR (500 MHz, DMSO-d$_6$) δ: 6.78 (s, 1H), 6.66 (d, J=8.06 Hz, 1H), 6.50 (d, J=8.06 Hz, 1H), 6.49 (s, 1H), 5.99 (s, 1H), 4.18 (s, 2H), 3.88 (s, 3H), 3.87 (s, 3H), 3.79 (s, 3H), 3.78 (s, 3H), 3.75 (s, 3H), 3.51 (s, 3H); $^{13}$C-NMR (125 MHz, DMSO-d$_6$) δ: 152.1, 148.8, 147.4, 145.9, 145.3, 137.3, 135.7, 131.9, 129.7, 122.8, 121.3, 120.5, 117.2, 114.1, 112.1, 112.0, 111.2, 60.4, 60.3, 56.0, 55.9, 55.8, 55.7, 40.3, 39.8.

Synthesis and Characterization of 2,3-dibromo-1-(2'-bromo-6'-(2"-bromo-4",5"-dimethoxybenzyl)-3',4'-dimethoxybenzyl)-4,5-dimethoxybenzene (7)

At room temperature, to a solution of 2,3-dibromo-1-(2'-bromo-6'-(3",4"-dimethoxybenzyl)-3',4'-dimethoxybenzyl)-4,5-dimethoxybenzene in CH$_2$Cl$_2$ was added dropwise bromine (mole ratio, bromine:2,3-dibromo-1-(2'-bromo-6'-(3",4"-dimethoxybenzyl)-3',4'-dimethoxybenzyl)-4,5-dimethoxybenzene=2:1). TLC was used to monitor the reaction. The solvent was evaporated and the residue was redissolved in CHCl$_3$. The organic phase was washed with 5% Na$_2$SO$_3$ for two times, and concentrated in vacuo. The residue was recrystallized in methanol to give white solid. Spectrum analysis verified the compound is 2,3-dibromo-1-(2'-bromo-6'-(2"-bromo-4",5"-dimethoxybenzyl)-3',4'-dimethoxybenzyl)-4,5-dimethoxybenzene.

The physical and chemical properties: m.p. 151-152° C., $^1$H-NMR (500 MHz, DMSO-d$_6$) δ: 6.97 (s, 1H), 6.56 (s, 1H), 6.41 (s, 1H), 6.16 (s, 1H), 4.23 (s, 1H), 3.86 (s, 3H), 3.83 (s, 3H), 3.80 (s, 3H), 3.76 (s, 3H), 3.70 (s, 3H), 3.57 (s, 3H); $^{13}$C-NMR (125 MHz, DMSO-d$_6$) δ: 152.2, 152.1, 148.5, 146.0, 146.0, 145.3, 135.9, 135.5, 130.5, 129.6, 122.6, 121.6, 117.,., 115.7, 114.9, 113.7, 113.5, 112.0, 60.5, 60.4, 56.1, 56.1, 56.0×2, 40.3, 39.6.

Scheme 4 shows the preparation of 3,4,6-tribromo-5-(2-bromo-3,4-dihydroxy-6-(propoxymethyl)benzyl)benzene-1,2-diol (8), 3,4,6-tribromo-5-(2-bromo-3,4-dihydroxy-6-(isopropoxymethyl)benzyl)benzene-1,2-diol (9), 3,4,6-tribromo-5-(2-bromo-6-(butoxymethyl)-3,4-dihydroxybenzyl)benzene-1,2-diol (10) and 3,4,6-tribromo-5-(2-bromo-3,4-dihydroxy-6-(isobutoxymethyl)benzyl)benzene-1,2-diol (11)

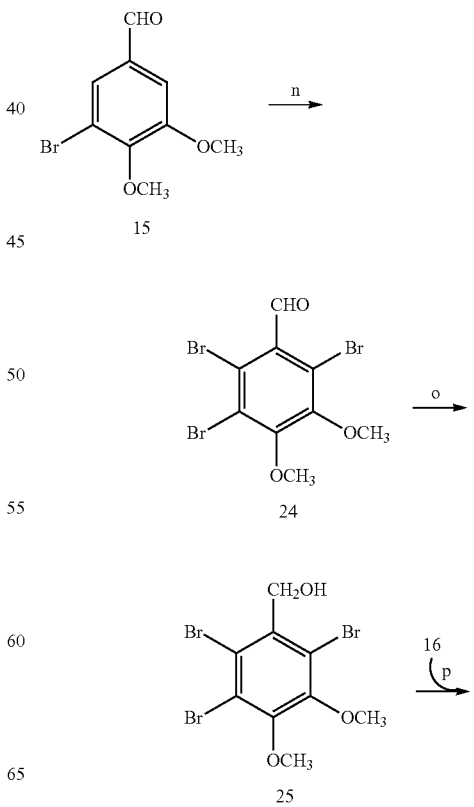

-continued

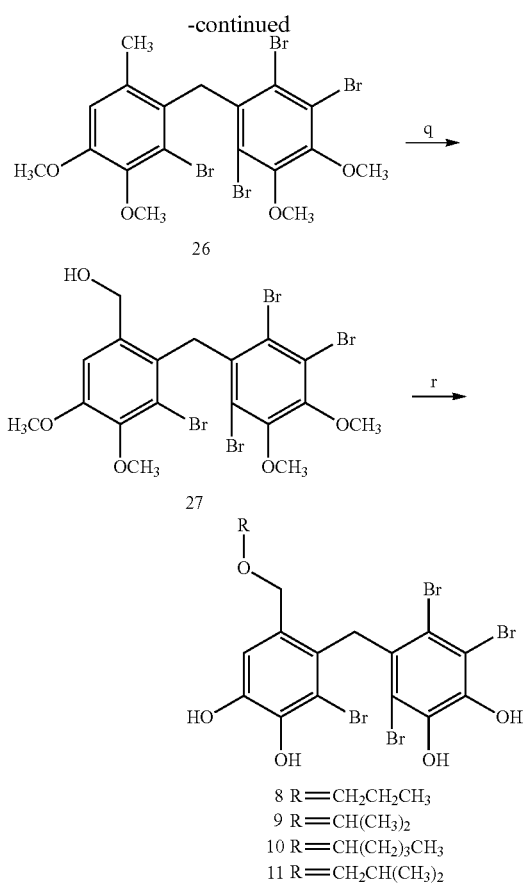

8 R=CH₂CH₂CH₃
9 R=CH(CH₃)₂
10 R=CH(CH₂)₃CH₃
11 R=CH₂CH(CH₃)₂

Scheme 4 (n) N-Bromosuccinimide, cond. $H_2SO_4$, 0° C.; (o) $NaBH_4$, MeOH, 0° C.; (p) $AlCl_3$, $CH_2Cl_2$, 0° C.; (q) N-Bromosuccinimide, AIBN, $CCl_4$, hv; $H_2O$, dioxane, reflux; (r) $BBr_3$, $CH_2Cl_2$, 0° C.; $H_3PO_4$, corresponding alcohol, 70~80° C.

Synthesis and Characterization of 2,3,6-tribromo-4,5-dimethoxybenzaldehyde (24)

Under 0° C. condition, to a stirred solution of 5-bromo-veratraldehyde in cond. $H_2SO_4$ was added N-Bromosuccinimide (mole ratio, 5-bromo-veratraldehyde:N-Bromosuccinimide=1:2~1:3). TLC was used to monitor the reaction. The mixture was poured into ice water. The organic layer was extracted with $CHCl_3$ for three times. The organic layer was washed with $Na_2CO_3$ solution and dried over anhydrous $MgSO_4$ and concentrated in vacuo. The residue was purified by column chromatography eluted with petroleum ether and ethyl acetate (30:1) to produce white solid. Spectrum analysis verified the compound is 2,3,6-tribromo-4,5-dimethoxybenzaldehyde.

The physical and chemical properties: m.p. 160-162° C. 1H NMR (500 MHz, CDCl3): δ 10.10 (s, 1H), 4.00 (s, 3H), 3.93 (s, 3H).

Synthesis and Characterization of 2,3,6-tribromo-4,5-dimethoxyphenyl-methanol (25)

Under ice bath condition, to a stirred solution of 2,3,6-tribromo-4,5-dimethoxybenzaldehyde in MeOH was added $NaBH_4$ (mole ratio, $NaBH_4$:2,3,6-tribromo-4,5-dimethoxybenzaldehyde=1:3~1:2). TLC was used to monitor the reaction. 10% HCl was added into the reaction to acidified pH=5-6, MeOH was evaporated and the residue was extracted with $CH_2Cl_2$. The organic layer was collected, dried over anhydrous $MgSO_4$ and concentrated in vacuo to give white solid. Spectrum analysis verified the compound is 2,3,6-tribromo-4,5-dimethoxyphenyl-methanol.

Synthesis and Characterization of 1,2,4-tribromo-3-(2-bromo-3,4-dimethoxy-6-methylbenzyl)-5,6-dimethoxybenzene (26)

Under ice bath condition, to a stirred solution of 5-bromo-3,4-dimethoxy-methylbenzene and 2,3,6-tribromo-4,5-dimethoxyphenyl-methanol in $CH_2Cl_2$ was added $AlCl_3$ (mole ratio, $AlCl_3$:5-bromo-3,4-dimethoxy-methylbenzene: 2,3,6-tribromo-4,5-dimethoxyphenyl-methanol=1:1:1) in portions. TLC was used to monitor the reaction. The mixture was poured into ice water. The organic layer was washed with 3% HCl three times, dried over anhydrous $MgSO_4$ and concentrated in vacuo. The residue was recrystallized from MeOH to give white solid. Spectrum analysis verified the compound is 1,2,4-tribromo-3-(2-bromo-3,4-dimethoxy-6-methylbenzyl)-5,6-dimethoxybenzene.

The physical and chemical properties: 1H NMR (500 MHz, CDCl3): δ 6.58 (s, 1H), 4.68 (s, 2H), 3.89 (s, 3H), 3.86 (s, 3H), 3.83 (s, 3H), 3.81 (s, 3H), 1.98 (s, 3H); $^{13}$C NMR (125 MHz, CDCl3): δ 151.2, 150.6, 150.4, 137.4, 133.5, 129.0, 126.5, 123.2, 122.8, 122.0, 121.8, 114.2, 60.5, 60.4, 56.0, 55.9, 43.3, 21.3.

Synthesis and Characterization of (3-bromo-4,5-dimethoxy-2-(2,3,6-tribromo-4,5-dimethoxybenzyl)phenyl)methanol (27)

Under hv condition, to a solution of catalyst AIBN or BPO and 1,2,4-tribromo-3-(2-bromo-3,4-dimethoxy-6-methylbenzyl)-5,6-dimethoxybenzene and in CCl4 (mass concentration 4~10%) was added NBS (mole ratio, AIBN or BPO: 1,2,4-tribromo-3-(2-bromo-3,4-dimethoxy-6-methylbenzyl)-5,6-dimethoxybenzene=1:100, NBS:1,2,4-tribromo-3-(2-bromo-3,4-dimethoxy-6-methylbenzyl)-5,6-dimethoxybenzene=1.1:1) with stirring. TLC was used to monitor the reaction. Then hv stopped. The precipitate was filtered off and the solvent was removed in vacuo to produce a brownish residue. The residue was purified by chromatography eluted with petroleum ether and ethyl acetate (8:1) to give white solid. The white solid (mass concentration 10~15%) and $K_2CO_3$ (mass concentration 5~10%) were dissolved in mixture of dixoane and $H_2O$ (volume ratio, 1:1) and the reaction was heated to 90-100° C. TLC was used to monitor the reaction. The mixture was extracted with $CHCl_3$. The organic layer was collected and concentrated in vacuo to give white solid. Spectrum analysis verified the compound is 3-bromo-4,5-dimethoxy-2-(2,3,6-tribromo-4,5-dimethoxybenzyl)phenyl-methanol.

The physical and chemical properties: 1H NMR (500 MHz, CDCl3): δ 7.02 (s, 1H), 4.69 (s, 2H), 4.36 (s, 2H), 3.89 (s, 3H), 3.87 (s, 3H), 3.86 (s, 3H), 3.82 (s, 3H); $^{13}$C NMR (125 MHz, CDCl3): δ 151.7, 150.6, 150.5, 145.6, 137.0, 136.2, 128.1, 123.0, 122.8, 122.0, 121.4 110.9, 63.0, 60.9, 60.7, 60.3, 56.0, 42.3.

Synthesis and Characterization of 3,4,6-tribromo-5-(2-bromo-3,4-dihydroxy-6-(propoxymethyl)benzyl)benzene-1,2-diol (8)

Under 0° C. condition, to a solution of 3-bromo-4,5-dimethoxy-2-(2,3,6-tribromo-4,5-dimethoxybenzyl)phenyl-methanol in $CH_2Cl_2$ (mass concentration 4-10%) was added dropwise $BBr_3$ (1 mol·L$^{-1}$ in $CH_2Cl_2$, mass ratio, $BBr_3$:3-bromo-4,5-dimethoxy-2-(2,3,6-tribromo-4,5-dimethoxybenzyl)phenyl-methanol=6:1~8:1). The reaction mixture stirred over night at room temperature. Then the mixture was poured into ice-cold water and extracted with ethyl acetate for three times. The organic layer was collected, and concentrated in vacuo. The residue was dissolved in n-propanol and added 1~2 mL 85% $H_3PO_4$. After refluxing for 1-2 hours, the n-propanol was removed in vacuo. The residue was purified by column chromatography eluted with petroleum ether and ethyl acetate (1:1) to produce yellow solid. Spectrum analysis verified the compound is 3,4,6-tribromo-5-(2-bromo-3,4-dihydroxy-6-(propoxymethyl)benzyl)benzene-1,2-diol The physical and chemical properties: $^1$H NMR (500 MHz, DMSO-$d_6$): δ 9.83 (s, 1H), 9.67 (s, 1H), 9.56 (s, 1H), 8.92 (s, 1H), 6.78 (s, 1H), 4.44 (s, 2H), 4.02 (s, 2H), 3.12 (t, J=6.63 Hz, 2H), 1.43 (m, 2H), 0.82 (t, J=9.69 Hz, 3H); $^{13}$C NMR (125 MHz, DMSO-$d_6$): δ 143.6, 143.4, 142.0, 131.3, 128.8, 126.7, 116.9, 114.7, 114.4, 114.3, 114.1, 71.1, 69.8, 41.6, 22.3, 10.5; HRESIMS m/z 614.7654 ([M—H]$^-$, $C_{17}H_{15}O_5Br_4$, calc 614.7653).

Synthesis and Characterization of 3,4,6-tribromo-5-(2-bromo-3,4-dihydroxy-6-(isopropoxymethyl)benzyl)benzene-1,2-diol (9)

Under 0° C. condition, to a solution of 3-bromo-4,5-dimethoxy-2-(2,3,6-tribromo-4,5-dimethoxybenzyl)phenylmethanol in $CH_2Cl_2$ (mass concentration 4-10%) was added dropwise BBr$_3$ (1 mol·L$^{-1}$ in $CH_2Cl_2$, mass ratio, BBr$_3$:3-bromo-4,5-dimethoxy-2-(2,3,6-tribromo-4,5-dimethoxybenzyl)phenyl-methanol=6:1~8:1). The reaction mixture stirred over night at room temperature. Then the mixture was poured into ice-cold water and extracted with ethyl acetate for three times. The organic layer was collected, and concentrated in vacuo. The residue was dissolved in iso-propanol and added 1-2 mL 85% $H_3PO_4$. After refluxing for 1-2 hours, the iso-propanol was removed in vacuo. The residue was purified by column chromatography eluted with petroleum ether and ethyl acetate (1:1) to produce yellow solid. Spectrum analysis verified the compound is 3,4,6-tribromo-5-(2-bromo-3,4-dihydroxy-6-(isopropoxymethyl)benzyl)benzene-1,2-diol.

The physical and chemical properties: $^1$H NMR (500 MHz, DMSO-$d_6$): δ 9.85 (s, 1H), 9.70 (s, 1H), 9.54 (s, 1H), 8.90 (s, 1H), 6.82 (s, 1H), 4.45 (s, 2H), 3.99 (s, 2H), 1.00 (d, J=6.06 Hz, 6H); $^{13}$C NMR (125 MHz, DMSO-$d_6$): δ 143.7, 143.6, 143.5, 141.7, 131.3, 129.3, 126.1, 117.0, 114.4, 114.1, 113.9, 70.3, 66.7, 41.7, 21.8; HRESIMS m/z 614.7646 ([M—H]$^-$, $C_{17}H_{15}O_5Br_4$, calc 614.7653).

Synthesis and Characterization of 3,4,6-tribromo-5-(2-bromo-6-(butoxymethyl)-3,4-dihydroxybenzyl)benzene-1,2-diol (9)

Under 0° C. condition, to a solution of 3-bromo-4,5-dimethoxy-2-(2,3,6-tribromo-4,5-dimethoxybenzyl)phenylmethanol in $CH_2Cl_2$ (mass concentration 4-10%) was added dropwise BBr$_3$ (1 mol·L$^{-1}$ in $CH_2Cl_2$, mass ratio, BBr$_3$:3-bromo-4,5-dimethoxy-2-(2,3,6-tribromo-4,5-dimethoxybenzyl)phenyl-methanol=6:1~8:1). The reaction mixture stirred over night at room temperature. Then the mixture was poured into ice-cold water and extracted with ethyl acetate for three times. The organic layer was collected, and concentrated in vacuo. The residue was dissolved in n-butyl alcohol and added 1~2 mL, 85% $H_3PO_4$. After refluxing for 1-2 hours, the n-butyl alcohol was removed in vacuo. The residue was purified by column chromatography eluted with petroleum ether and ethyl acetate (1:1) to produce yellow solid. Spectrum analysis verified the compound is 3,4,6-tribromo-5-(2-bromo-6-(butoxy methyl)-3,4-dihydroxybenzyl)benzene-1,2-diol.

The physical and chemical properties: $^1$H NMR (500 MHz, DMSO-$d_6$): δ 9.83 (s, 1H), 9.67 (s, 1H), 9.56 (s, 1H), 8.93 (s, 1H), 6.77 (s, 1H), 4.44 (s, 2H), 4.02 (s, 2H), 3.16 (t, J=6.53, 2H), 1.39 (m, 2H), 1.25 (m, 2H), 0.82 (t, J=7.35 Hz, 3H); $^{13}$C NMR (125 MHz, DMSO-$d_6$): δ 143.6, 143.4, 142.0, 131.3, 128.8, 126.7, 116.9, 114.7, 114.4, 114.3, 114.1, 69.8, 69.1, 41.6, 31.1, 18.8, 13.7; HRESIMS m/z 628.7826 ([M—H]$^-$, $C_{18}H_{17}O_5Br_4$, calc 628.7809).

Synthesis and Characterization of 3,4,6-tribromo-5-(2-bromo-3,4-dihydroxy-6-(isobutoxymethyl)benzyl)benzene-1,2-diol (10)

Under 0° C. condition, to a solution of 3-bromo-4,5-dimethoxy-2-(2,3,6-tribromo-4,5-dimethoxybenzyl)phenylmethanol in $CH_2Cl_2$ (mass concentration 4-10%) was added dropwise BBr$_3$ (1 mol·L$^{-1}$ in $CH_2Cl_2$, mass ratio, BBr$_3$:3-bromo-4,5-dimethoxy-2-(2,3,6-tribromo-4,5-dimethoxybenzyl)phenyl-methanol=6:1~8:1). The reaction mixture stirred over night at room temperature. Then the mixture was poured into ice-cold water and extracted with ethyl acetate for three times. The organic layer was collected, and concentrated in vacuo. The residue was dissolved in isobutanol and added 1~2 mL 85% $H_3PO_4$. After refluxing for 1-2 hours, the isobutanol was removed in vacuo. The residue was purified by column chromatography eluted with petroleum ether and ethyl acetate (1:1) to produce yellow solid. Spectrum analysis verified the compound is 3,4,6-tribromo-5-(2-bromo-3,4-dihydroxy-6-(isobutoxymethyl)benzyl)benzene-1,2-diol.

The physical and chemical properties: $^1$H NMR (500 MHz, DMSO-$d_6$): δ 9.83 (s, 1H), 9.68 (s, 1H), 9.57 (s, 1H), 8.93 (s, 1H), 6.79 (s, 1H), 4.44 (s, 2H), 4.05 (s, 2H), 2.95 (d, J=6.51 Hz, 2H), 1.17 (m, 1H), 0.81 (d, J=6.67 Hz, 6H); $^{13}$C NMR (125 MHz, DMSO-$d_6$): δ 143.6, 143.4, 142.0, 131.3, 128.9, 126.7, 116.9, 114.6, 114.4, 114.2, 114.1, 76.2, 70.0, 41.5, 27.8, 19.2; HRESIMS m/z 628.7839 ([M—H]$^-$, $C_{18}H_{17}O_5Br_4$, calc 628.7809).

Scheme 5 shows the preparation of 3,4,6-tribromo-5-(2-bromo-3,4-dihydroxy-6-methyl benzyl)benzene-1,2-diol

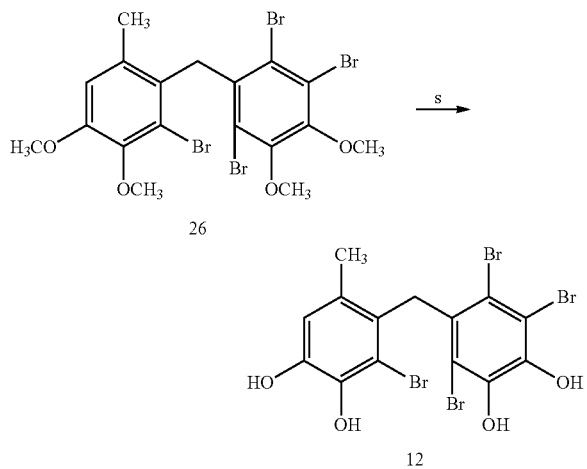

Scheme 5 (n) BBr$_3$, $CH_2Cl_2$, 0° C.

Synthesis and Characterization of 3,4,6-tribromo-5-(2'-bromo-3',4'-dihydroxy-6'-methylbenzyl)benzene-1,2-diol Under 0° C. condition, to a solution of 1,2,4-tribromo-3-(2'-bromo-3',4'-dimethoxy-6'-methylbenzyl)-5,6-dimethoxybenzene In $CH_2Cl_2$, with mass concentration 4~10% was added dropwise 1 mol·L$^{-1}$ BBr$_3$ dichloromethane solution. Molar ratio of BBr$_3$ and 1,2,4-tribromo-3-(2'-bromo-3',4'-dimethoxy-6'-methylbenzyl)-5,6-dimethoxybenzene was 6:1~8:1. The reaction mixture stirred over night at room temperature. Then the mixture was poured into ice-cold water and extracted with ethyl acetate for three times. The organic layer was collected, and concentrated in vacuo. The residue was purified by column chromatography eluted with CHCl$_3$:MeOH=30:1 to produce yellowish solid. Spectrum analysis verified the compound is 3,4,6-tribromo-5-(2'-bromo-3',4'-dihydroxy-6'-methylbenzyl)benzene-1,2-diol.

The physical and chemical properties: $^1$H NMR (500 MHz, DMSO-$d_6$): δ 6.47 (s, 1H), 4.45 (s, 2H), 2.08 (s, 3H); $^{13}$C NMR (125 MHz, DMSO-$d_6$): δ 143.7, 143.6, 143.4, 140.8, 131.5, 127.5, 126.6, 117.0, 116.9, 114.9, 114.5, 114.1, 42.7, 20.0; HRESIMS m/z 556.7235 ([M—H]$^-$, $C_{14}H_9O_4Br_4$, calc 556.7234).

All of the PTP1B inhibitors are compounds with PTP1B inhibitory activity. The compounds has been implicated in the negative regulation of insulin signal transduction pathways, enhanced insulin sensitivity and modulated blood glucose, and could be used for treating type 2 diabetes mellitus.

PTP1B Inhibition Assay

Construct human recombinant PTP1B engineering bacteria hGST-PTP1B-BL21 via molecular biology methods, and purify it through GST-tagged affinity chromatography. The principle is that the product pNP, which is enzymolysis of pNPP by PTP1B, absorbs at 405 nm. The activity of PTP1B inhibition can be measured by calculating the quantity of pNP.

The advantages of this invention are as follows:

The target compounds are with potent PTP1B inhibitory activities, and are promising for treatment of insulin resistance T2DM. The invention has implemented total synthesis of target compounds. The starting materials are cheap and commercial available, the procedures are simple and yields are acceptable. So the preparation of these compounds have good scale-up perspective.

EXAMPLES

Example 1

Synthesis and Characterization of (2'-bromo-6'-(dibromomethyl)-3',4'-dimethoxyphenyl)-(2,3-dibromo-4,5-dimethoxyphenyl)-methanone (1)

(1) Synthesis and Characterizaion of 5-bromo-vanilline

To a solution of vanillin (7.6 g, 50 mmol) in MeOH (60 mL) was added dropwise $Br_2$ (2.8 mL, 50 mmol) over a 2 h period at 0° C. The mixture was warm to room temperature for another 1 h. Then cooling to 0° C., water (25 mL) was poured over a 20 min period and resulted in the precipitation of white solid. The mixture was stirred for further 15 min. The precipitate was filtered, washed with ice water and dried to give 10.7 g of white solid. Spectrum analysis verified the compound is 5-Br-vanillin.

The physical and chemical properties: m.p. 160~162° C. $^1$H NMR (500 MHz, CDCl$_3$) δ: 9.78 (s, 1H), 7.64 (d, J=1.65 Hz, 1H), 7.36 (d, J=1.65 Hz, 2H), 3.98 (s, 3H); $^{13}$C-NMR (125 MHz, CDCl$_3$) δ: 189.5 (CHO), 148.9 (C), 147.7 (C), 130.1, 130.0 (C), 108.2 (C), 108.1 (CH), 56.6 (CH$_3$).

(2) Synthesis and Characterization of 5-bromo-veratraldehyde

At room temperature, to a suspension of 5-Br-vanillin (4.26 g, 18 mmol) and K$_2$CO$_3$ (3.84 g, 24 mmol) in DMF (40 mL) was added CH$_3$I (1.7 mL, 33 mmol) dropwise. After stirring for 24 h, 20% brine (100 mL) was added to quench the reaction. The mixture was extracted with tert-butyl methyl ether (3×100 mL). The organic layer was collected, washed with 20% brine, dried over anhydrous MgSO$_4$ and concentrated in vacuo to give 4.2 g white solid. Spectrum analysis verified the compound is 5-bromo-veratraldehyde.

The physical and chemical properties: m.p. 60~62° C. $^1$H-NMR (500 MHz, CDCl$_3$) δ: 9.84 (s, 1H), 7.64 (s, 1H), 7.38 (s, 1H), 3.94 (s, 3H), 3.93 (s, 3H); $^{13}$C-NMR (125 MHz, CDCl$_3$) δ: 189.7 (CHO), 154.2 (C), 151.8 (C), 133.1 (C), 128.7 (CH), 117.9 (CH), 110.2 (C), 60.8 (CH$_3$), 56.2 (CH$_3$).

(3) Synthesis and Characterization of 5-bromo-3,4-dimethoxy-methylbenzene

At room temperature, to a solution of 5-bromo-veratraldehyde (29.4 g, 120 mmol) in diglycol (200 mL) was added 80% hydrazine hydrate (13 mL). TLC was used to monitor the reation. Then 24 g KOH was added and the mixture was heated to 120° C. for 2 h. After cooling, the resulting mixture was poured into water (200 mL), and extracted with 200 mL CH$_2$Cl$_2$ for three times. The organic layer was collected, washed with 1 mol/L HCl (3×200 mL), dried over anhydrous Na$_2$SO$_4$ and concentrated in vacuo to give 24 g colorless oil. Spectrum analysis verified the compound is 5-bromo-3,4-dimethoxy-methylbenzene The physical and chemical properties: $^1$H-NMR (500 MHz, CDCl$_3$) δ: 6.94 (s, 1H), 6.65 (s, 1H), 3.84 (s, 3H), 3.82 (s, 3H), 2.28 (s, 3H); $^{13}$C-NMR (125 MHz, CDCl$_3$) δ: 153.3 (C), 144.1 (C), 135.1 (C), 124.8 (CH), 117.1 (C), 112.5 (CH), 60.4 (CH$_3$), 55.9 (CH$_3$), 21.,0 (CH$_3$).

(4) Synthesis and Characterization of 5,6-dibromo-veratraldehyde

At room temperature, to a solution of 5-bromo-veratraldehyde (31 g, 126 mmol) in AcOH (220 mL) was added dropwise Br$_2$ (12.6 mL, 244 mmol) and iron powder (100 mg). The mixture was heated at 60° C. and stirred for 5 h. After cooling to room temperature, the iron powder was filtered and the filtrate was removed in vacuo. The residue was redissolved in CHCl$_3$ (200 mL), and washed with 5% Na$_2$SO$_3$ (2×200 mL). The organic layer was collected, and concentrated in vacuo. The residue was recrystallized in acetone to give 27 g white needle crystal. Spectrum analysis verified the compound is 5,6-dibromo-veratraldehyde.

The physical and chemical properties: m.p. 128-130° C. $^1$H-NMR (500 MHz, CDCl$_3$) δ: 10.27 (s, 1H), 7.48 (s, 1H), 3.94 (s, 3H), 3.92 (s, 3H); $^{13}$C-NMR (125 MHz, CDCl$_3$) δ: 191.5 (CHO), 152.8 (C), 131.0 (C), 122.8 (C), 121.9 (C), 111.7 (CH), 60.8 (CH$_3$), 56.3 (CH$_3$).

(5) Synthesis and Characterization of 5,6-dibromo-veratric acid 5,6-dibromo-veratraldehyde (38 g, 117 mmol) and NaHCO$_3$ (5.7 g, 80 mmol) and water (300 mL) were placed in a 500 mL three-necked round bottom flask. The suspension was heated to 90° C. and added KMnO$_4$ (19.0 g, 100 mmol) in three portions. TLC was used to monitor the reaction and the MnO$_2$ was filtered. The filtrate was acidified. The white precipitate was filtered and washed with water to give 36.3 g white solid. Spectrum analysis verified the compound is 5,6-dibromo-veratric acid.

The physical and chemical properties: m.p. 180-181° C.; $^1$H NMR (500 MHz, CD$_3$OCD$_3$): δ 7.39 (s, 1H, H-2), 3.90 (s, 3H, H-8), 3.87 (s, 3H, H-9); $^{13}$C NMR (125 MHz, CD$_3$OCD$_3$): δ 169.2 (C-7), 153.6 (C-4), 150.9 (C-3), 132.8 (C-1), 127.5 (C-6), 123.8 (C-5), 114.5 (C-2), 60.9 (C-8), 56.9 (C-9).

(6) Synthesis and Characterization of (2-bromo-3,4-dimethoxy-6-methylphenyl)-(2,3-dibromo-4,5-dimethoxyphenyl)-methanone Under ice bath condition, to a solution of 5,6-dibromo-veratraldehyde (2.4 g, 7 mmol) in TFAA (10 mL) was added 85% H$_3$PO$_4$ (0.5 mL) and 5-bromo-3,4-dimethoxy-methylbenzene (1.71 g, 7.5 mmol). The mixture was heated to 60° C. TLC was used to monitor the reaction. Then the mixture was poured into crushed ice and extracted with CHCl$_3$. The organic layer was collected dried over anhydrous MgSO$_4$ and concentrated in vacuo. The residue was recrystallized in EtOH to give 3.5 g white crystal. Spectrum analysis verified the compound is (2-bromo-3,4-dimethoxy-6-methylphenyl)-(2,3-dibromo-4,5-dimethoxyphenyl)-methanone.

The physical and chemical properties: m.p. 86-88° C.; $^1$H NMR (500 MHz, CDCl$_3$): δ 7.16 (s, 1H, H-6), 6.74 (s, 1H, H-5'), 3.91 (s, 3H, H-9), 3.90 (s, 3H, H-11), 3.81 (s, 3H, H-10), 3.79 (s, 3H, H-12), 2.22 (s, 3H, H-8); $^{13}$C NMR (125 MHz, CDCl$_3$): δ 194.2 (C-7), 154.0 (C-4), 152.0 (C-4'), 150.8 (C-5), 144.6 (C-3'), 135.7 (C-1), 133.7 (C-1'), 133.0 (C-6'), 124.3 (C-2), 116.3 (C-2'), 115.5 (C-3), 115.1 (C-6), 113.8 (C-5'), 60.6 (C-9,11), 56.3 (C-10), 56.0 (C-12), 20.2 (C-8).

(7) Synthesis and Characterization of (2-bromo-6-(dibromomethyl)-3,4-dimethoxyphenyl)-(2,3-dibromo-4,5-dimethoxyphenyl)-methanone (2-bromo-3,4-dimethoxy-6-methylphenyl)-(2,3-dibromo-4,5-dimethoxyphenyl)-methanone (4.29 g, 7.8 mmol), AIBN (43 mg) and NBS (3.45 g, 19.4 mmol) were dissolved in CCl$_4$ (50 mL). The mixture was heated to reflux and TLC was used to monitor the reaction. Then the precipitate was filtered off and the solvent was removed in vacuo to produce a brownish residue. The residue was purified by chromatography eluted with petroleum ether and ethyl acetate (20:1) to give 1.95 g white solid. Spectrum analysis verified the compound is (2-bromo-6-(dibromomethyl)-3,4-dimethoxyphenyl)-(2,3-dibromo-4,5-dimethoxyphenyl)-methanone The physical and chemical properties: m.p. 166-169° C.; $^1$H NMR (500 MHz, CDCl$_3$): δ 7.58 (s, 1H), 7.07 (s, 1H), 6.66 (s, 1H), 4.03 (s, 3H), 3.93 (s, 3H), 3.87 (s, 3H), 3.78 (s, 3H); $^{13}$C NMR (125 MHz, CDCl$_3$): δ 192.8 (CO), 155.1, 152.0, 151.2, 147.6, 137.4, 135.2, 129.2, 124.7, 116.8, 115.1. 114.4, 113.5, 60.8 (2×CH$_3$), 56.4 (2×CH$_3$), 36.7 (CHBr$_2$); HRMS: [M+H]$^+$ calcd for C$_{18}$H$_{16}$O$_5$Br$_5$: 706.6915, found: 706.6882.

Example 2

Synthesis and Characterization of 3,4-dibromo-5-[2'-bromo-3',4'-dihydroxy-6'-(propoxymethyl)-benzyl]-benzene-1,2-diol (2), 3,4-dibromo-5-[2'-bromo-3',4'-dihydroxy-6'-(isopropoxymethyl)-benzyl]-benzene-1,2-diol (3), 3,4-dibromo-5-[2'-bromo-6'-(butoxymethyl)-3',4'-dihydroxy-benzyl]-benzene-1,2-diol (4), 3,4-dibromo-5-[2'-bromo-3',4'-dihydroxy-6'-(isobutoxymethyl)-benzyl]-benzene-1,2-diol (5) and 3,4-dibromo-5-(2-bromo-6-(sec-butoxymethyl)-3,4-dihydroxybenzyl)benzene-1,2-diol (6)

(1) Synthesis and Characterization of 5,6-dibromo-3,4-dimethoxy-phenyl-methanol

Under ice bath condition, to a stirred solution of 5,6-dibromo-veratraldehyde (72 g, 222 mmol) in MeOH (400 mL) was added NaBH$_4$ (2.2 g, 5.5 mmol). TLC was used to monitor the reaction. Then 10% HCl was added to adjust the reaction to weak acidity. MeOH was evaporated and extracted with CH$_2$Cl$_2$. The organic layer was collected, dried over anhydrous MgSO$_4$ and concentrated in vacuo to give 66 g white solid. Spectrum analysis verified the compound is 5,6-dibromo-3,4-dimethoxy-phenyl-methanol.

The physical and chemical properties: m.p. 91-93° C. $^1$H-NMR (500 MHz, CDCl$_3$) δ: 7.01 (s, 1H), 4.71 (s, 2H), 3.88 (s, 3H), 3.84 (s, 3H); $^{13}$C-NMR (125 MHz, CDCl$_3$) δ: 152.7 (C), 146.8 (C), 137.3 (C), 121.7 (C), 114.9 (C), 111.5 (CH), 65.9 (CH$_2$), 60.5 (CH$_3$), 56.2 (CH$_3$).

(2) Synthesis and Characterization of 2,3-dibromo-1-(2'-bromo-3',4'-dimethoxy-6'-methylbenzyl)-4,5-dimethoxy benzene Under ice bath condition, to a stirred solution of 5-bromo-3,4-dimethoxy-methylbenzene (23.1 g, 100 mmol) and 5,6-dibromo-3,4-dimethoxy-phenyl-methanol (32.6 g, 100 mmol) in CH$_2$Cl$_2$ (300 mL) was added AlCl$_3$ (13.4 g, 100 mmol). TLC was used to monitor the reaction. Then the mixture was poured into ice water (100 mL). The organic layer was collected and washed with 3% HCl (3×200 mL), dried over anhydrous MgSO$_4$ and concentrated in vacuo. The residue was recrystallized from MeOH to give 48 g white solid. Spectrum analysis verified the compound is 2,3-dibromo-1-(2'-bromo-3',4'-dimethoxy-6'-methylbenzyl)-4,5-dimethoxy benzene.

The physical and chemical properties: m.p. 114-117° C. $^1$H-NMR (500 MHz, CDCl$_3$) δ: 6.76 (s, 1H), 6.15 (s, 1H), 4.19 (s, 2H), 3.89 (s, 3H), 3.84 (s, 3H), 3.81 (s, 3H), 3.56 (s, 3H), 2.17 (s, 3H); $^{13}$C-NMR (125 MHz, CDCl$_3$) δ: 152.5 (C), 152.0 (C), 146.1 (C), 144.9 (C), 135.8 (C), 134.3 (C), 129.6 (C), 122.1 (C), 121.7 (C), 117.6 (C), 113.8 (CH), 111.7 (CH), 60.4 (2×CH$_3$), 56.1 (CH$_3$), 56.0 (CH$_3$), 40.5 (CH$_2$), 20.6 (CH$_3$).

(3) Synthesis and Characterization of (3-bromo-2-(2',3'-dibromo-4',5'-dimethoxybenzyl)-4,5-dimethoxyphenyl)-methanol Under hv condition, to a solution of AIBN (350 mg) and 2,3-dibromo-1-(2'-bromo-3',4'-dimethoxy-6'-methylbenzyl)-4,5-dimethoxy benzene (35 g, 65 mmol) in CCl$_4$ (400 mL) was added NBS (12.7 g, 71 mmol). TLC was used to monitor the reaction. The precipitate was filtered off and the solvent was removed in vacuo to produce a brownish residue. The residue was purified by chromatography eluted with petroleum ether and ethyl acetate (8:1) to give benzyl bromide as white solid. The white solid and K$_2$CO$_3$ (mass ratio 2:1) were dissolved in mixture of dixoane and H$_2$O (60 mL, volume ratio 1:1) and the reaction was heated to 90° C. TLC was used to monitor the reaction. The mixture was extracted with CHCl$_3$ (100 mL) and H$_2$O (100 mL). The organic layer was collected and concentrated in vacuo to give 12.5 g white solid. Spectrum analysis verified the compound is (3-bromo-2-(2',3'-dibromo-4',5'-dimethoxybenzyl)-4,5-dimethoxyphenyl)-methanol.

The physical and chemical properties: m.p. 164-166° C. $^1$H-NMR (500 MHz, CDCl$_3$) δ: 7.09 (s, 1H), 6.14 (s, 1H), 4.52 (s, 2H), 4.22 (s, 2H), 3.91 (s, 3H), 3.86 (s, 3H), 3.79 (s, 3H), 3.55 (s, 3H); $^{13}$C-NMR (125 MHz, CDCl$_3$) δ: 152.4 (2×C), 146.1 (C), 145.9 (C), 136.6 (C), 135.8 (C), 128.7 (C), 122.5 (C), 121.7 (C), 117.4 (C), 111.8 (CH), 111.4 (CH), 63.0 (CH$_2$), 60.4 (2×CH$_3$), 56.0 (2×CH$_3$), 39.2 (CH$_2$).

(4) Synthesis and Characterization of 3,4-dibromo-5-(2-bromo-3,4-dihydroxy-6-(propoxymethyl)benzyl)benzene-1,2-diol (3bromo-2-(2',3'-dibromo-4',5'-dimethoxybenzyl)-4,5-dimethoxyphenyl)-methanol (0.9 g) was dissolved in 20 mL CH$_2$Cl$_2$, then BBr$_3$ (1 mol·L$^{-1}$ in CH$_2$Cl$_2$, 16 mL) was added dropwise while stirring at 0° C. The reaction mixture stirred over night at room temperature. Then the solution was poured into ice water (50 mL) and extracted with EtOAc (3×50 mL). The organic layer was collected, and concentrated in vacuo. The residue was dissolved in n-propanol (15 mL) and H$_3$PO$_4$ (1 mL). After refluxing for 2 hours, the n-propanol was removed in vacuo. The residue was purified by column chromatography eluted with petroleum ether and EtOAc (1:1) to produce 0.5 g yellow solid. Spectrum analysis verified the compound is 3,4-dibromo-5-(2-bromo-3,4-dihydroxy-6-(propoxymethyl)benzyl)benzene-1,2-diol The physical and chemical properties: $^1$H NMR (500 MHz, DMSO-d$_6$): δ 9.75 (s, 1H), 9.69 (s, 1H), 9.27 (s, 1H), 9.14 (s, 1H), 6.88 (s, 1H), 6.05 (s, 1H), 4.17 (s, 2H), 3.99 (s, 2H), 3.26 (t, J=6.52, 2H), 1.14 (m, J=, 2H), 0.79 (t, J=7.36, 3H); 13C NMR (125 MHz, DMSO-d6): δ 144.9 (C), 144.3 (C), 142.5 (2×C), 130.5 (C), 129.0 (C), 127.5 (C), 115.4, 114.6 (C), 114.3, 113.9 (C), 112.9 (C), 71.2 (CH$_2$), 70.3 (CH$_2$), 38.3 (CH$_2$), 22.2 (CH$_2$), 10.4 (CH$_3$); EIMS m/z 544/542/540/538 [M]$^+$ (1/3/3/1), 484/482/480/478 (2/7/7/2), 467/465/463/461 (2/6/6/2), 403/401/399 (7/15/7), 322/320 (19/18), 82/80 (42/43), 59 (100); HRMS: [M—H]$^-$ calcd for C$_{17}$H$_{16}$O$_5$$^{79}$Br$_3$: 536.8548; found: 536.8570.

(5) Synthesis and Characterization of 3,4-dibromo-5-(2-bromo-3,4-dihydroxy-6-(isopropoxymethyl)benzyl)benzene-1,2-diol (3-bromo-2-(2',3'-dibromo-4',5'-dimethoxybenzyl)-4,5-dimethoxyphenyl)-methanol (0.9 g) was dissolved in 20 mL CH$_2$Cl$_2$, then BBr$_3$ (1 mol·L$^{-1}$ in CH$_2$Cl$_2$, 16 mL) was added dropwise while stirring at 0° C. The reaction mixture stirred over night at room temperature. Then the solution was poured into ice water (50 mL) and extracted with EtOAc (3×50 mL). The organic layer was collected, and concentrated in vacuo. The residue was dissolved in iso-propanol (15 mL) and H$_3$PO$_4$ (1 mL). After refluxing for 2 hours, the iso-propanol was removed in vacuo. The residue was purified by column chromatography eluted with petroleum etherand EtOAc (1:1) to produce 0.5 g yellow solid. Spectrum analysis verified the compound is 3,4-dibromo-5-(2-bromo-3,4-dihydroxy-6-(isopropoxymethyl)benzyl)benzene-1,2-diol The physical and chemical properties: $^1$H NMR (500 MHz, DMSO-d$_6$): δ 9.72 (s, 1H), 9.69 (s, 1H), 9.26 (s, 1H), 9.11 (s, 1H), 6.88 (s, 1H), 6.05 (s, 1H), 4.15 (s, 2H), 3.98 (s, 2H), 3.51 (m, J=6.43, 2H), 1.02 (d, J=6.43, 6H); $^{13}$C NMR (125 MHz, DMSO-d$_6$): δ 144.9 (C), 144.3 (C), 142.5 (C), 142.4 (C), 130.5 (C), 129.3 (C), 127.5 (C), 115.4 (CH), 114.5 (C), 114.3 (C), 113.9 (CH), 112.9 (C), 79.1 (CH), 67.6 (CH$_2$), 38.3 (CH$_2$), 21.7 (2×CH$_3$); EIMS m/z 544/542/540/538[M]$^+$ (1/3/3/1), 484/482/480/478 (2/7/7/2), 467/465/463/461 (2/6/6/2), 403/401/399 (5/10/5), 322/320 (10/9), 82/80 (98/100), 59 (30); HRMS: [M—H]$^-$ calcd for C$_{17}$H$_{16}$O$_5$$^{79}$Br$_3$: 536.8548; found: 536.,8525.

(6) Synthesis and Characterization of 3,4-dibromo-5-(2-bromo-6-(butoxymethyl)-3,4-dihydroxybenzyl)benzene-1,2-diol (3-bromo-2-(2',3'-dibromo-4',5'-dimethoxybenzyl)-4,5-dimethoxyphenyl)-methanol (0.9 g) was dissolved in 20 mL CH$_2$Cl$_2$, then BBr$_3$ (1 mol·L$^{-1}$ in CH$_2$Cl$_2$, 16 mL) was added dropwise while stirring at 0° C. The reaction mixture stirred over night at room temperature. Then the solution was poured into ice water (50 mL) and extracted with EtOAc (3×50 mL). The organic layer was collected, and concentrated in vacuo. The residue was dissolved in n-butyl alcohol (15 mL) and H$_3$PO$_4$ (1 mL). After refluxing for 2 hours, the n-butyl alcohol was removed in vacuo. The residue was purified by column chromatography eluted with petroleum etherand EtOAc (1:1) to produce 0.4 g yellow solid. Spectrum analysis verified the compound is 3,4-dibromo-5-(2-bromo-6-(butoxymethyl)-3,4-dihydroxybenzyl)benzene-1,2-diol.

The physical and chemical properties: $^1$H NMR (500 MHz, DMSO-d$_6$): δ 9.75 (s, 1H), 9.69 (s, 1H), 9.27 (s, 1H), 9.15 (s, 1H), 6.87 (s, 1H), 6.04 (s, 1H), 4.16 (s, 2H), 3.98 (s, 2H), 3.29 (t, J=6.44, 2H), 1.36 (m, 2H), 1.22 (m, 2H), 0.80 (t, J=7.35, 3H); $^{13}$C NMR (125 MHz, DMSO-d$_6$): δ 144.9 (C), 144.2 (C), 142.5 (2×C), 130.5 (C), 129.0 (C), 127.5 (C), 115.4 (CH), 114.6 (C), 114.3 (CH), 113.9 (C), 112.9 (C), 70.4 (CH$_2$), 69.2 (CH$_2$), 38.3 (CH$_2$), 31.1 (CH$_2$), 18.7 (CH$_2$), 13.6 (CH$_3$); EIMS m/z 484/482/480/478 (2/7/7/2), 467/465/463/461 (2/6/6/2), 403/401/399 (5/10/5), 322/320 (13/12), 82/80 (18/18), 59 (100); HRMS: [M—H]$^-$ calcd for C$_{18}$H$_{18}$O$_5$$^{79}$Br$_3$: 550.8704; found: 550.8688.

(7) Synthesis and Characterization of 3,4-dibromo-5-(2-bromo-3,4-dihydroxy-6-(isobutoxymethyl)benzyl)benzene-1,2-diol (3-bromo-2-(2',3'-dibromo-4',5'-dimethoxybenzyl)-4,5-dimethoxyphenyl)-methanol (0.9 g) was dissolved in 20 mL CH$_2$Cl$_2$, then BBr$_3$ (1 mol·L$^{-1}$ in CH$_2$Cl$_2$, 16 mL) was added dropwise while stirring at 0° C. The reaction mixture stirred over night at room temperature. Then the solution was poured into ice water (50 mL) and extracted with EtOAc (3×50 mL). The organic layer was collected, and concentrated in vacuo. The residue was dissolved in iso-butanol (15 mL) and H$_3$PO$_4$ (1 mL). After refluxing for 2 hours, the iso-butanol was removed in vacuo. The residue was purified by column chromatography eluted with petroleum etherand EtOAc (1:1) to produce 0.35 g yellow solid. Spectrum analysis verified the compound is 3,4-dibromo-5-(2-bromo-3,4-dihydroxy-6-(isobutoxymethyl)benzyl)benzene-1,2-diol.

The physical and chemical properties: $^1$H NMR (500 MHz, DMSO-d$_6$): δ 9.75 (s, 1H), 9.69 (s, 1H), 9.27 (s, 1H), 9.15 (s, 1H), 6.88 (s, 1H), 6.04 (s, 1H), 4.16 (s, 2H), 3.98 (s, 2H), 3.08 (d, J=6.48, 2H), 1.68 (m, 1H), 0.78 (d, J=6.68, 6H); $^{13}$C NMR (125 MHz, DMSO-d$_6$): δ 144.9 (C), 144.2 (C), 142.5 (2×C), 130.5 (C), 129.0 (C), 127.5 (C), 115.4 (CH), 114.6 (C), 114.3 (CH), 113.9 (C), 113.0 (C), 76.4 (CH$_2$), 70.6 (CH$_2$), 38.3 (CH$_2$), 27.8 (CH), 19.1 (2×CH$_3$); EIMS m/z 558/556/554/552 [M]$^+$ (1/3/3/1), 484/482/480/478 (5/15/14/5), 467/465/463/461 (3/9/10/3), 404/402/400 (5/10/7), 403/401/399 (10/21/10), 322/320 (27/25), 82/80 (99/100), 57 (40); HRMS: [M—H]$^-$ calcd for C$_{18}$H$_{18}$O$_5$$^{79}$Br$_3$: 550.8704; found: 550.8680.

(8) Synthesis and Characterization of 3,4-dibromo-5-(2'-bromo-6'-(sec-butoxymethyl)-3',4'-dihydroxybenzyl)benzene-1,2-diol Under 0° C. condition, (3-bromo-2-(2',3'-dibromo-4',5'-dimethoxybenzyl)-4,5-dimethoxyphenyl)-methanol (0.9 g) in 20 mL CH$_2$Cl$_2$ was added dropwise 1 mol·L$^{-1}$ BBr$_3$ dichloromethane solution (16 mL). The reaction mixture stirred over night at room temperature. Then the mixture was poured into 50 mL ice-cold water and extracted with 50 mL EtOAc for three times. The organic layer was collected, and concentrated in vacuo. The residue was dissolved in 15 mL sec-butyl alcohol. Then 1 mL H$_3$PO$_4$ was added. After refluxing for 2 h, the sec-butyl alcohol was removed in vacuo. The residue was purified by column chromatography eluted with petroleum ether:ethyl acetate=1:1 to produce yellow solid 0.2 g. Spectrum analysis verified the compound is 3,4-dibromo-5-(2'-bromo-6'-(sec-butoxymethyl)-3',4'-dihydroxybenzyl)benzene-1,2-diol.

The physical and chemical properties: $^1$H NMR (500 MHz, DMSO-d$_6$): δ 9.73 (s, 1H), 9.70 (s, 1H), 9.28 (s, 1H), 9.13 (s, 1H), 6.88 (s, 1H), 6.04 (s, 1H), 4.20 (d, J=11.36, 1H), 4.10 (d, J=11.36, 1H), 3.99 (s, 2H), 3.29 (m, 1H) 1.35 (m, 2H), 1.00 (d, J=6.11, 3H), 0.77 (t, J=7.40, 3H); $^{13}$C NMR (125 MHz, DMSO-d$_6$): δ 144.9, 144.2, 142.5, 142.4, 130.5, 129.4, 127.4, 115.5, 114.5, 114.3, 113.9, 113.0, 75.2, 67.8, 38.3, 28.4, 18.6, 9.3; HRESIMS m/z 550.8728 ([M—H]$^-$, C$_{18}$H$_{18}$O$_5$Br$_3$, calc 550.8704).

Example 3

Synthesis and Characterization of 2,3-dibromo-1-[2'-bromo-6'-(2"-bromo-4",5"-dimethoxybenzyl)-3',4'-dimethoxybenzyl]-4,5-dimethoxybenzene (7)

(1) Synthesis and Characterization of 2,3-dibromo-1-(2'-bromo-6'-(3",4"-dimethoxybenzyl)-3',4'-dimethoxybenzyl)-4,5-dimethoxybenzene Under ice bath condition, to a solution of veratrole (0.69 g, 5 mmol) and (3-bromo-2-(2',3'-dibromo-4',5'-dimethoxybenzyl)-4,5-dimethoxyphenyl)-methanol (2.78 g, 5 mmol) in $CH_2Cl_2$ was added $AlCl_3$ (0.8 g, 7 mmol). TLC was used to monitor the reaction. The mixture was poured into ice-water. The organic phase was washed with 3% HCl for three times, then dried over anhydrous $MgSO_4$ and concentrated in vacuo. The residue was recrystallized from MeOH to give 2.8 g white solid. Spectrum analysis verified the compound is 2,3-dibromo-1-(2'-bromo-6'-(3",4"-dimethoxybenzyl)-3',4'-dimethoxybenzyl)-4,5-dimethoxybenzene.

The physical and chemical properties: m.p. 138-139° C. $^1$H-NMR (500 MHz, DMSO-$d_6$) δ: 6.78 (s, 1H), 6.66 (d, J=8.06 Hz, 1H), 6.50 (d, J=8.06 Hz, 1H), 6.49 (s, 1H), 5.99 (s, 1H), 4.18 (s, 2H), 3.88 (s, 3H), 3.87 (s, 3H), 3.79 (s, 3H), 3.78 (s, 3H), 3.75 (s, 3H), 3.51 (s, 3H); $^{13}$C-NMR (125 MHz, DMSO-$d_6$) δ: 152.1, 148.8, 147.4, 145.9, 145.3, 137.3, 135.7, 131.9, 129.7, 122.8, 121.3, 120.5, 117.2, 114.1, 112.1, 112.0, 111.2, 60.4, 60.3, 56.0, 55.9, 55.8, 55.7, 40.3, 39.8.

(2) Synthesis and Characterization of 2,3-dibromo-1-(2'-bromo-6'-(2"-bromo-4",5"-dimethoxybenzyl)-3',4'-dimethoxybenzyl)-4,5-dimethoxybenzene At room temperature, to a solution of 2,3-dibromo-1-(2'-bromo-6'-(3",4"-dimethoxybenzyl)-3',4'-dimethoxybenzyl)-4,5-dimethoxybenzene (1 g, 1.48 mmol) in $CH_2Cl_2$ (20 mL) was added dropwise bromine (0.15 mL, 2.96 mmol). The reaction lasted 1-2 h. TLC was used to monitor the reaction. The solvent was evaporated and the residue was redissolved in $CHCl_3$. The organic phase was washed with 5% $Na_2SO_3$ for two times, and concentrated in vacuo. The residue was recrystallized in MeOH to give 0.844 g white solid. Spectrum analysis verified the compound is 2,3-dibromo-1-(2'-bromo-6'-(2"-bromo-4",5"-dimethoxybenzyl)-3',4'-dimethoxybenzyl)-4,5-dimethoxybenzene.

The physical and chemical properties: m.p. 151-152° C. $^1$H-NMR (500 MHz, DMSO-$d_6$) δ: 6.97 (s, 1H), 6.56 (s, 1H), 6.41 (s, 1H), 6.16 (s, 1H), 4.23 (s, 1H), 3.86 (s, 3H), 3.83 (s, 3H), 3.80 (s, 3H), 3.76 (s, 3H), 3.70 (s, 3H), 3.57 (s, 3H); $^{13}$C-NMR (500 MHz, DMSO-$d_6$) δ: 152.2, 152.1, 148.5, 146.0, 146.0, 145.3, 135.9, 135.5, 130.5, 129.6, 122.6, 121.6, 117.6, 115.7, 114.9, 113.7, 113.5, 112.0, 60.5, 60.4, 56.1, 56.1, 56.0×2, 40.3, 39.6.

Example 4

Synthesis and Characterizaion of 3,4,6-tribromo-5-(2-bromo-3,4-dihydroxy-6-(propoxymethyl)benzyl)benzene-1,2-diol (8), 3,4,6-tribromo-5-(2-bromo-3,4-dihydroxy-6-(isopropoxymethyl)benzyl)benzene-1,2-diol (9), 3,4,6-tribromo-5-(2-bromo-6-(butoxymethyl)-3,4-dihydroxybenzyl)benzene-1,2-diol (10), and 3,4,6-tribromo-5-(2-bromo-3,4-dihydroxy-6-(isobutoxymethyl)benzyl)benzene-1,2-diol (11)

(1) Synthesis and Characterization of 2,3,6-tribromo-4,5-dimethoxy-benzaldehyde

Under 0° C. condition, to a solution of 5-bromo-veratraldehyde (2.45 g) in cond. $H_2SO_4$ (20 mL) was added NBS (3.9 g). TLC was used to monitor the reaction. Then the mixture was poured into ice-cold water (100 mL) and extracted with $CHCl_3$ for three times. The organic layer was collected, washed with $Na_2CO_3$ solution, dried over anhydrous $MgSO_4$ and concentrated in vacuo. The residue was purified by column chromatography eluted with petroleum ether and ethyl acetate (30:1) to produce white solid 3.2 g. Spectrum analysis verified the compound is 2,3,6-tribromo-4,5-dimethoxy-benzaldehyde.

The physical and chemical properties: m.p. 160~162° C., $^1$H NMR (500 MHz, CDCl$_3$): δ 10.10 (s, 1H), 4.00 (s, 3H), 3.93 (s, 3H).

(2) Synthesis and Characterization of 2,3,6-tribromo-4,5-dimethoxy-phenyl-methanol Under ice bath condition, to a stirred solution of 2,3,6-tribromo-4,5-dimethoxy-benzaldehyde (4.03 g) in 30 mL MeOH was added $NaBH_4$ (0.15 g). TLC was used to monitor the reaction. 10% HCl was added into the reaction to acidified pH=5-6. MeOH was evaporated and the residue was extracted with $CH_2Cl_2$ (50 mL). The organic layer was collected, dried over anhydrous $MgSO_4$ and concentrated in vacuo to give white solid 3.64 g. Spectrum analysis verified the compound is 2,3,6-tribromo-4,5-dimethoxy-phenyl-methanol.

(3) Synthesis and Characterization of 1,2,4-tribromo-3-(2'-bromo-3',4'-dimethoxy-6'-methylbenzyl)-5,6-dimethoxybenzene 3-bromo-4,5-dimethoxy-methylbenzene (2.31 g) and 2,3,6-tribromo-4,5-dimethoxy-phenyl-methanol (4.04 g) were dissolved in 30 mL $CH_2Cl_2$. Under ice bath condition, to this solution was added 1.34 g $AlCl_3$. TLC was used to monitor the reaction. The mixture was poured into 50 mL ice water. The organic layer was washed with 3% HCl (50 mL) for three times, dried over anhydrous $MgSO_4$ and concentrated in vacuo. The residue was recrystallized from MeOH to give white solid 4.6 g. Spectrum analysis verified the compound is 1,2,4-tribromo-3-(2'-bromo-3',4'-dimethoxy-6'-methylbenzyl)-5,6-dimethoxybenzene.

The physical and chemical properties: $^1$H NMR (500 MHz, CDCl$_3$): δ 6.58 (s, 1H), 4.68 (s, 2H), 3.89 (s, 3H), 3.86 (s, 3H), 3.83 (s, 3H), 3.81 (s, 3H), 1.98 (s, 3H). $^{13}$C NMR (125 MHz, CDCl$_3$): δ 151.2, 150.6, 150.4, 137.4, 133.5, 129.0, 126.5, 123.2, 122.8, 122.0, 121.8, 114.2, 60.5, 60.4, 56.0, 55.9, 43.3, 21.3.

(4) Synthesis and Characterization of (3-bromo-4,5-dimethoxyphenyl-2-(2',3',6'-tribromo-4',5'-dimethoxybenzyl)phenyl)-methanol.

Under hv condition, to a solution of AIBN (62 mg) and 1,2,4-tribromo-3-(2'-bromo-3',4'-dimethoxy-6'-methylbenzyl)-5,6-dimethoxybenzene (6.18 g) in 60 mL $CCl_4$ was added 1.96 g NBS in batches. The mixture was turned to red when NBS was added. The next batch of NBS was not added until red disappears. After the last batch of NBS was added, the mixture continued to light for 15-30 min. Then hv stopped. The precipitate was filtered off and the solvent was removed in vacuo. The residue was purified by chromatography eluted with petroleum ether:ethyl acetate=8:1 to give white solid. The white solid and 4 g $K_2CO_3$ were dissolved in mixture of 40 mL dixoane and 40 mL $H_2O$. The mixture was heated to 90-100° C. TLC was used to monitor the reaction. The mixture was added five-fold volume of 100 mL $CHCl_3$ and 100 mL $H_2O$. The organic layer was collected and concentrated in vacuo to give white solid 2.8 g. Spectrum analysis verified the compound is (3-bromo-4,5-dimethoxyphenyl-2-(2',3',6'-tribromo-4',5'-dimethoxybenzyl)phenyl)-methanol.

The physical and chemical properties: $^1$H NMR (500 MHz, CDCl$_3$): δ 7.02 (s, 1H), 4.69 (s, 2H), 4.36 (s, 2H), 3.89 (s, 3H), 3.87 (s, 3H), 3.86 (s, 3H), 3.82 (s, 3H); $^{13}$C NMR (125 MHz, CDCl$_3$): δ 151.7, 150.6, 150.5, 145.6, 137.0, 136.2, 128.1, 123.0, 122.8, 122.0, 121.4, 110.9, 63.0, 60.9, 60.7, 60.3, 56.0, 42.3.

(5) Synthesis and Characterization of 3,4,6-tribromo-5-(2-bromo-3,4-dihydroxy-6-(propoxymethyl)benzyl)benzene-1,2-diol Under 0° C. condition, to a solution of (3-bromo-4,5-dimethoxyphenyl-2-(2',3',6'-tribromo-4',5'-dimethoxybenzyl)phenyl)-methanol (0.64 g) in 10 mL $CH_2Cl_2$ was added dropwise 1 mol·L$^{-1}$ BBr$_3$ dichloromethane solution (6 mL). The reaction mixture stirred over night at room temperature. Then the mixture was poured into 30 mL ice-cold water and extracted with EtOAc (30 mL) for three times. The organic layer was collected, and concentrated in vacuo. The residue was dissolved in 10 mL n-propanol. Then 1 mL 85% H$_3$PO$_4$ was added. After refluxing for 2 h, the solvent n-propanol was removed in vacuo. The residue was purified by column chromatography eluted with petroleum ether:ethyl acetate=1:1 to produce yellow solid 0.48 g. Spectrum analysis verified the compound is 3,4,6-tribromo-5-(2-bromo-3,4-dihydroxy-6-(propoxymethyl)benzyl)benzene-1,2-diol The physical and chemical properties: $^1$H NMR (500 MHz, DMSO-d$_6$): δ 9.83 (s, 1H), 9.67 (s, 1H), 9.56 (s, 1H), 8.92 (s, 1H), 6.78 (s, 1H), 4.44 (s, 2H), 4.02 (s, 2H), 3.12 (t, J=6.63 Hz, 2H), 1.43 (m, 2H), 0.82 (t, J=9.69 Hz, 3H); $^{13}$C NMR (125 MHz, DMSO-d$_6$): δ 143.6, 143.4, 142.0, 131.3, 128.8, 126.7, 116.9, 114.7, 114.4, 114.3, 114.1, 71.1, 69.8, 41.6, 22.3, 10.5; HRESIMS m/z 614.7654 ([M—H]$^-$, C$_{17}$H$_{15}$O$_5$Br$_4$, calc 614.7653).

(6) Synthesis and Characterization of 3,4,6-tribromo-5-(2-bromo-3,4-dihydroxy-6-(isopropoxymethyl)benzyl)benzene-1,2-diol Under 0° C. condition, to a solution of (3-bromo-4,5-dimethoxyphenyl-2-(2',3',6'-tribromo-4',5'-dimethoxybenzyl)phenyl)-methanol (0.64 g) in 10 CH$_2$Cl$_2$ was added dropwise 1 mol·L$^{-1}$ BBr$_3$ dichloromethane solution (6 mL). The reaction mixture stirred over night at room temperature. Then the mixture was poured into 30 mL ice-cold water and extracted with EtOAc (30 mL for three times. The organic layer was collected, and concentrated in vacuo. The residue was dissolved in 10 mL iso-propanol. Then 1 mL 85% H$_3$PO$_4$ was added. After refluxing for 2 h, the solvent isopropanol was removed in vacuo. The residue was purified by column chromatography eluted with petroleum ether:ethyl acetate=1:1 to produce yellow solid 0.45 g. Spectrum analysis verified the compound is 3,4,6-tribromo-5-(2-bromo-3,4-dihydroxy-6-(isopropoxymethyl)benzyl)benzene-1,2-diol.

The physical and chemical properties: $^1$H NMR (500 MHz, DMSO-d$_6$): δ 9.85 (s, 1H), 9.70 (s, 1H), 9.54 (s, 1H), 8.90 (s, 1H), 6.82 (s, 1H), 4.45 (s, 2H), 3.99 (s, 2H), 1.00 (d, J=6.06 Hz, 6H); $^{13}$C NMR (125 MHz, DMSO-d$_6$): δ 143.7, 143.6, 143.5, 141.7, 131.3, 129.3, 126.1, 117.0, 114.4, 114.1, 113.9, 70.3, 66.7, 41.7, 21.8; HRESIMS m/z 614.7646 ([M—H]$^-$, C$_{17}$H$_{15}$O$_5$Br$_4$, calc 614.7653).

(7) Synthesis and Characterization of 3,4,6-tribromo-5-(2-bromo-6-(butoxymethyl)-3,4-dihydroxybenzyl)benzene-1,2-diol Under 0° C. condition, to a solution of (3-bromo-4,5-dimethoxyphenyl-2-(2',3',6'-tribromo-4',5'-dimethoxybenzyl)phenyl)-methanol (0.64 g) in 10 mL CH$_2$Cl$_2$ was added dropwise 1 mol·L$^{-1}$ BBr$_3$ dichloromethane solution (6 mL). The reaction mixture stirred over night at room temperature. Then the mixture was poured into 30 mL ice-cold water and extracted with EtOAc (30 mL) for three times. The organic layer was collected, and concentrated in vacuo. The residue was dissolved in 10 mL n-butyl alcohol. Then 1 mL 85% H$_3$PO$_4$ was added. After refluxing for 2 h, the solvent n-butyl alcohol was removed in vacuo. The residue was purified by column chromatography eluted with petroleum ether:ethyl acetate=1:1 to produce yellow solid 0.44 g. Spectrum analysis verified the compound is 3,4,6-tribromo-5-(2-bromo-6-(butoxymethyl)-3,4-dihydroxybenzyl)benzene-1,2-diol.

The physical and chemical properties: $^1$H NMR (500 MHz, DMSO-d$_6$): δ 9.83 (s, 1H), 9.67 (s, 1H), 9.56 (s, 1H), 8.93 (s, 1H), 6.77 (s, 1H), 4.44 (s, 2H), 4.02 (s, 2H), 3.16 (t, J=6.53 Hz, 2H), 1.39 (m, 2H), 1.25 (m, 2H), 0.82 (t, J=7.35 Hz, 3H); $^{13}$C NMR (125 MHz, DMSO-d$_6$): δ 143.6, 143.4, 142.0, 131.3, 128.8, 126.7, 116.9, 114.7, 114.4, 114.3, 114.1, 69.8, 69.1, 41.6, 31.1, 18.8, 13.7; HRESIMS m/z 628.7826 ([M—H]$^-$, C$_{18}$H$_{17}$O$_5$Br$_4$, calc 628.7809).

(8) Synthesis and Characterization of 3,4,6-tribromo-5-(2-bromo-3,4-dihydroxy-6-(isobutoxymethyl)benzyl)benzene-1,2-diol Under 0° C. condition, to a solution of (3-bromo-4,5-dimethoxyphenyl-2-(2',3',6'-tribromo-4',5'-dimethoxybenzyl)phenyl)-methanol (0.64 g) in 10 mL CH$_2$Cl$_2$ was added dropwise 1 mol·L$^{-1}$ BBr$_3$ dichloromethane solution (6 mL). The reaction mixture stirred over night at room temperature. Then the mixture was poured into 30 mL ice-cold water and extracted with EtOAc (30 mL) for three times. The organic layer was collected, and concentrated in vacuo. The residue was dissolved in 10 mL isobutanol. Then 1 mL 85% H$_3$PO$_4$ was added. After refluxing for 2 h, the solvent isobutanol was removed in vacuo. The residue was purified by column chromatography eluted with petroleum ether:ethyl acetate=1:1 to produce yellow solid 0.43 g. Spectrum analysis verified the compound is 3,4,6-tribromo-5-(2-bromo-3,4-dihydroxy-6-(isobutoxymethyl)benzyl)benzene-1,2-diol.

The physical and chemical properties: $^1$H NMR (500 MHz, DMSO-d$_6$): δ 9.83 (s, 1H), 9.68 (s, 1H), 9.57 (s, 1H), 8.93 (s, 1H), 6.79 (s, 1H), 4.44 (s, 2H), 4.05 (s, 2H), 2.95 (d, J=6.51 Hz, 2H), 1.17 (m, 1H), 0.81 (d, J=6.67 Hz, 6H); $^{13}$C NMR (125 MHz, DMSO-d$_6$): δ 143.6, 143.4, 142.0, 131.3, 128.9, 126.7, 116.9, 114.6, 114.4, 114.2, 114.1, 76.2, 70.0, 41.5, 27.8, 19.2; HRESIMS m/z 628.7839 ([M—H]$^-$, C$_{18}$H$_{17}$O$_5$Br$_4$, calc 628.7809).

Example 5

Synthesis and Characterization of 3,4,6-tribromo-5-(2'-bromo-3',4'-dihydroxy-6'-methylbenzyl)benzene-1,2-diol (12)

Under 0° C. condition, to a solution of 1,2,4-tribromo-3-(2'-bromo-3',4'-dimethoxy-6'-methylbenzyl)-5,6-dimethoxybenzene (0.62 g) in 10 mL CH$_2$Cl$_2$ was added dropwise 1 mol·L$^{-1}$ BBr$_3$dichloromethane solution. The reaction mixture stirred over night at room temperature. Then the mixture was poured into 30 mL ice-cold water and extracted with 30 mL EtOAc for three times. The organic layer was collected, and concentrated in vacuo. The residue was purified by column chromatography eluted with CHCl$_3$: MeOH=30:1 to produce yellowish solid 0.48 g. Spectrum analysis verified the compound is 3,4,6-tribromo-5-(2'-bromo-3',4'-dihydroxy-6'-methylbenzyl)benzene-1,2-diol.

The physical and chemical properties: $^1$H NMR (500 MHz, DMSO-d$_6$): δ 6.47 (s, 1H), 4.45 (s, 2H), 2.08 (s, 3H); $^{13}$C-NMR (125 MHz, DMSO-d$_6$): δ 143.7, 143.6, 143.4, 140.8, 131.5, 127.5, 126.6, 117.0, 116.9, 114.9, 114.5, 114.1, 42.7, 20.0; HRESIMS m/z 556.7235 ([M—H]$^-$, C$_{14}$H$_9$O$_4$Br$_4$, calc 556.7234).

Example 6

PTP1B Inhibitory Assay

Compounds 1-12 were dissolved in DMSO. 2 μL of samples were placed into the system (50 mM Tris-HCl, pH 6.5, 2 mM pNPP, 2% DMSO, 30 nM hGST-PTP1B). DMSO was distributed as negative control and Na$_3$VO$_4$ was positive control. The reaction was at 30° C. and monitored at 405 nm for 3 min. Inhibitory rate was calculated according to the following formula:

$$\% \text{ inhibition} = 100\% \times [(V_{sample} - V_{DMSO})/(V_{DMSO} - V_{DMSO})]$$

The results are shown in Table 1.
TABLE 1
| Compds | Inhibitory Ratio (%) of PTP1B | | IC$_{50}$ (μg/mL) |
| --- | --- | --- | --- |
| | Inhibition (%) | | |
| | 20 μg/mL | 5 μg/mL | |
| 1 | 101.4 | 47.85 | 1.31 |
| 2 | 86.15 | 55.70 | 1.08 |
| 3 | 93.89 | 68.24 | 0.34 |
| 4 | 64.56 | 27.17 | ND |
| 5 | 96.25 | 48.30 | 0.83 |
| 6 | 96.50 | 42.40 | 1.01 |
| 7 | 101.02 | ND | ND |
| 8 | 98.81 | 42.40 | 1.01 |
| 9 | 98.52 | ND | ND |
| 10 | 99.04 | ND | ND |
| 11 | 100.94 | ND | ND |
| 12 | 57.67 | ND | ND |
The results showed that all of the compounds exhibit potent PTP1B inhibition, and are promising for treatment of T2DM.
The invention claimed is:
1. A PTP1B inhibitor selected from:
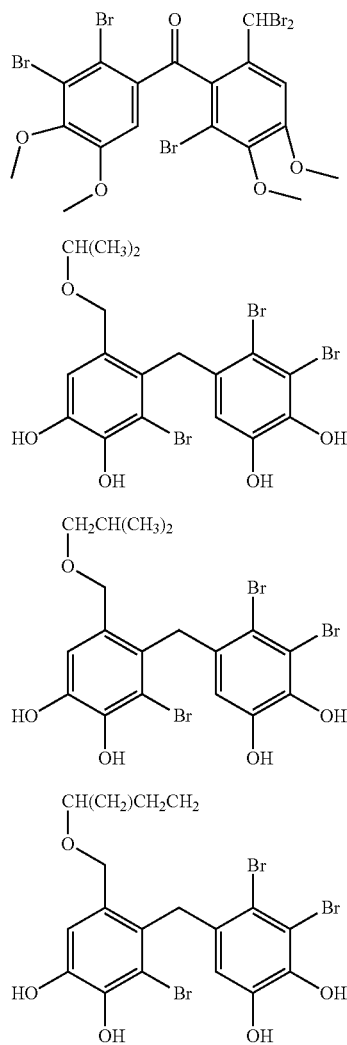
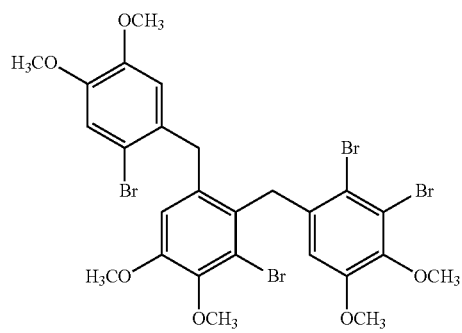
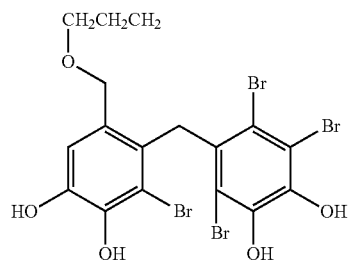
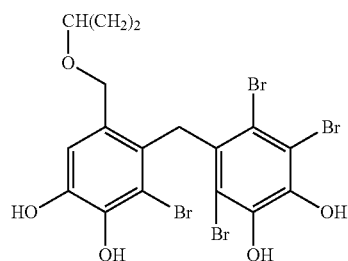
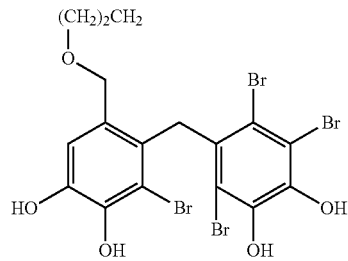
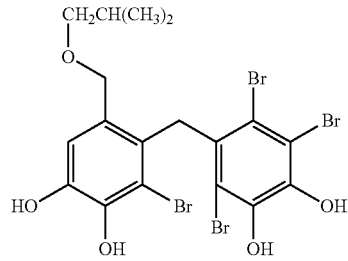
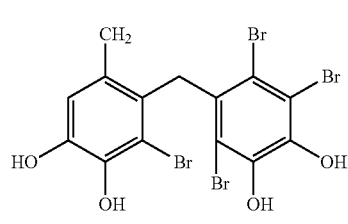
or mixtures thereof.

2. A method for preparing the PTP1B inhibitor according to claim 1, wherein the synthetic route for each of the twelve compounds are as follows:

(1) Synthetic route of compound 1

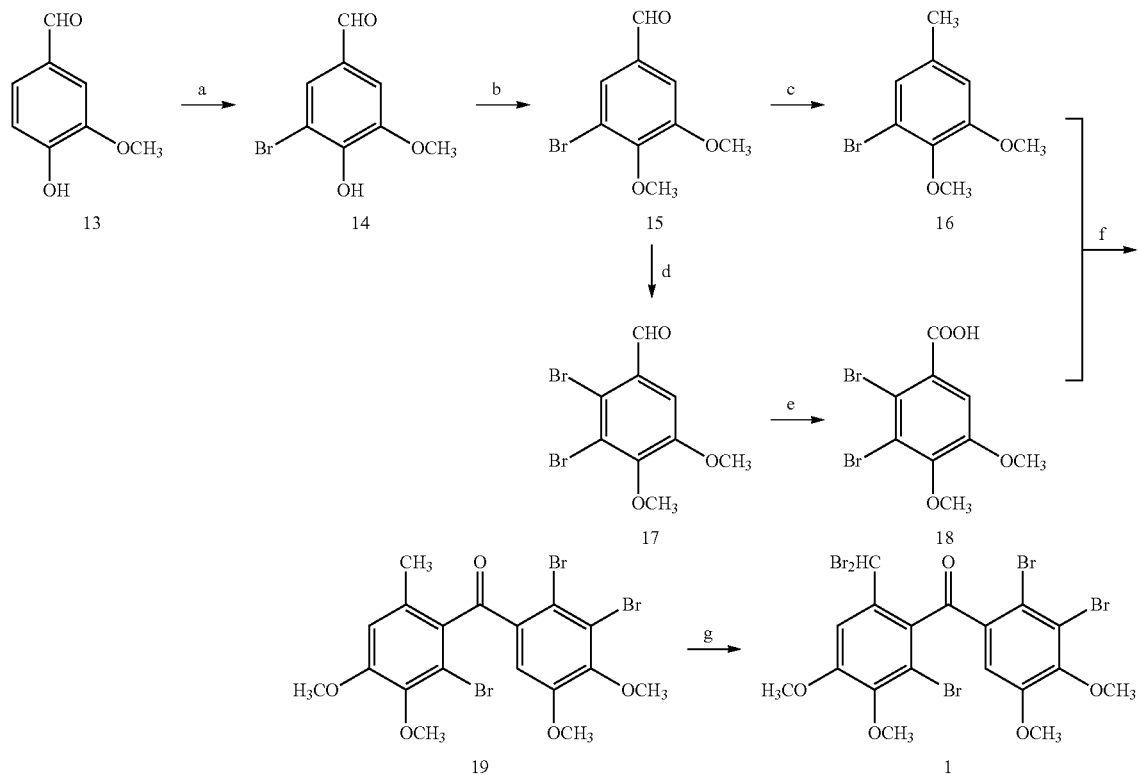

wherein the synthetic route for compound 1 includes Scheme 1 where (a) includes bromine and compound 13 (molar ratio is 1:1), MeOH, ice bath condition; (b) includes Methyl iodide and compound 14 (molar ratio is 1:1-1:1.5), $K_2CO_3$, DMF as solvent, room temperature; (c) includes a solution of compound 15 in diglycol (mass concentration of compound 15: 10-15%), mass concentration 80% hydrazine hydrate solution, KOH, 110-120° C.; (d) includes bromine and compound 15 (molar ratio is 2:1-3:1), acetic acid, 60-70° C.; and (e) includes $KMnO_4$, water, 90° C.; (f) Trifluoroacetic anhydride, $H_3PO_4$, 0-60° C.; and where (g) includes N-Bromosuccinimide, AIBN, $CCl_4$, hv.;

(2) Synthetic route of compounds 3, 5 and 6:

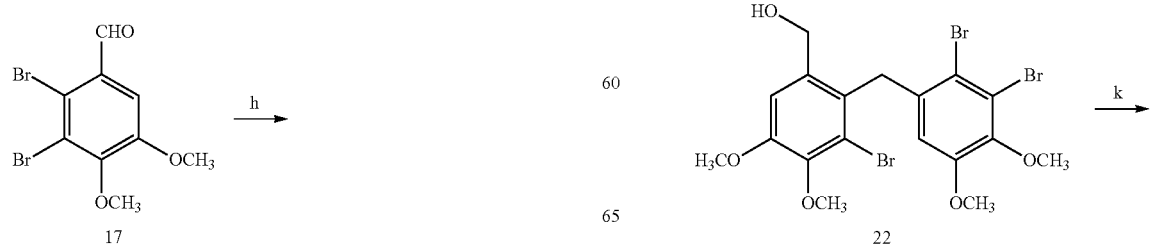

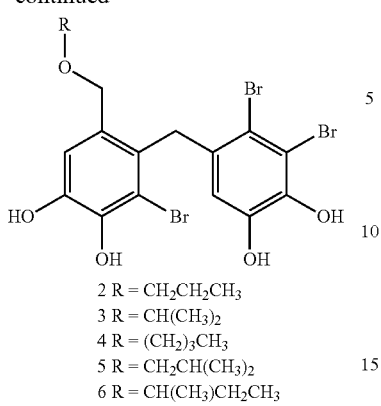

2 R = CH₂CH₂CH₃
3 R = CH(CH₃)₂
4 R = (CH₂)₃CH₃
5 R = CH₂CH(CH₃)₂
6 R = CH(CH₃)CH₂CH₃ wherein the synthetic route for compounds 2, 3, 4, 5 and 6 includes Scheme 2 where (h) includes NaBH₄, MeOH, 0° C.; (i) includes AlCl₃, CH₂Cl₂, 0° C.; (j) includes N-Bromosuccinimide, CCl₄, hv; H₂O, dioxane, reflux; and (k) includes BBr₃, CH₂Cl₂, 0° C.; H₃PO₄, R—OH where R is —CH(CH₃)₂, —CH₂CH(CH₃)₂ or —CH(CH₃)CH₂CH₃, 70-80° C.;

(3) Synthetic route of compound 7

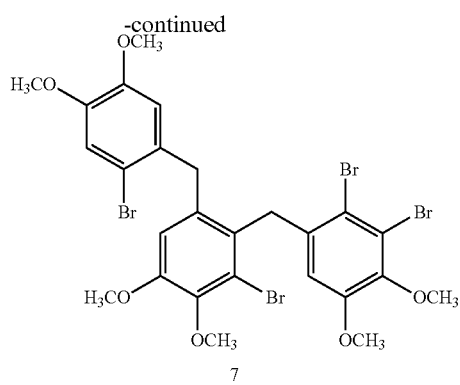

wherein the synthetic route for compound 7 includes Scheme 3 where (l) includes AlCl₃, CH₂Cl₂, room temperature; and (m) includes Bromine, CH₂Cl₂;

(4) Synthetic route of compound 8, 9, 10 and 11

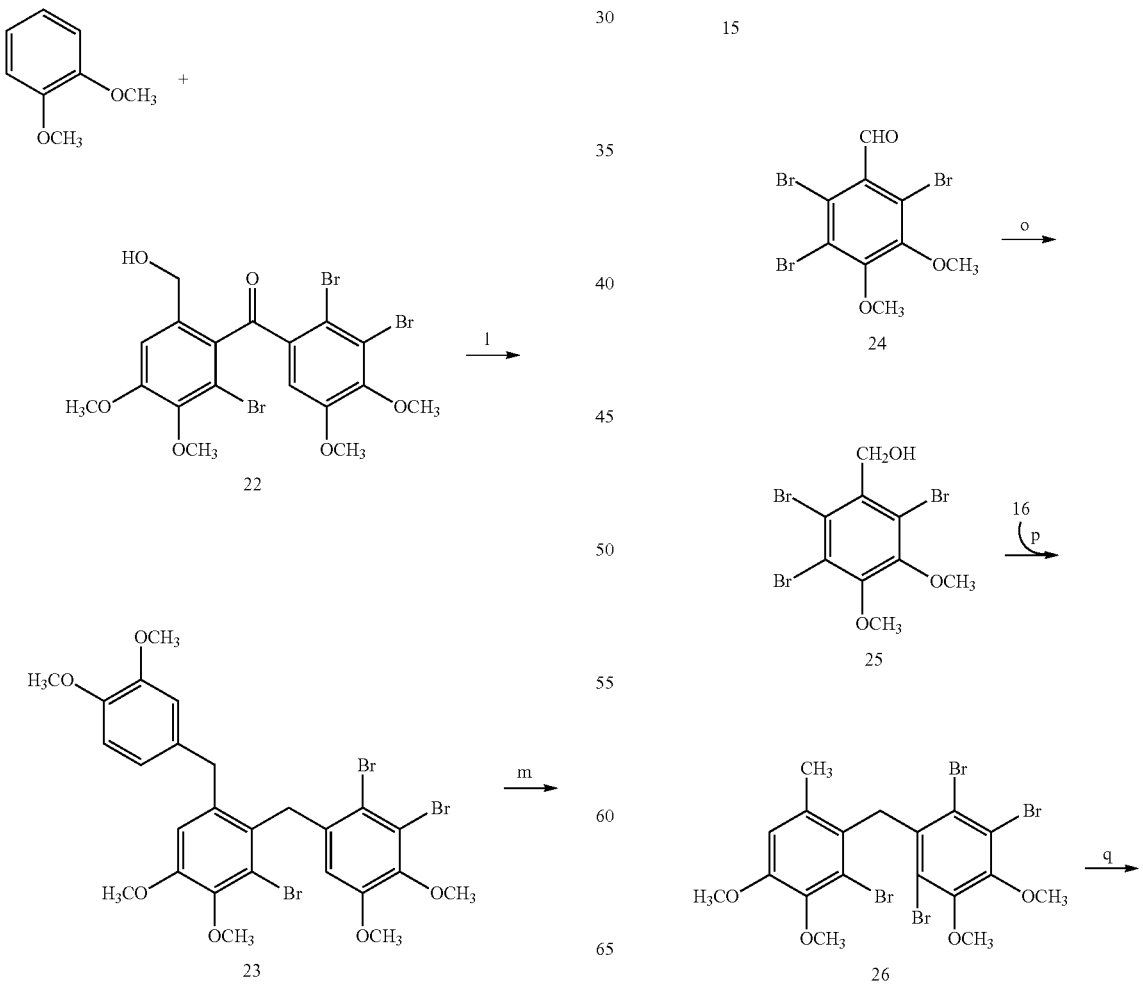

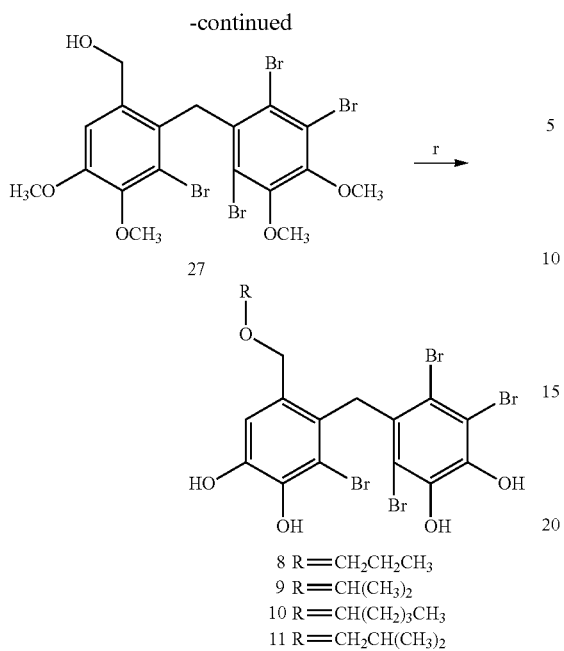

8 R=CH₂CH₂CH₃
9 R=CH(CH₃)₂
10 R=CH(CH₂)₃CH₃
11 R=CH₂CH(CH₃)₂ wherein the synthetic route for compounds 8, 9, 10 and 11 includes Scheme 4 where (n) includes N-Bromosuccinimide, cond. $H_2SO_4$, 0° C.; (o) includes $NaBH_4$, MeOH, 0° C.; (p) $AlCl_3$, $CH_2Cl_2$, 0° C.; (q) N-Bromosuccinimide, $CCl_4$, hv; $H_2O$, dioxane, reflux; (r) $BBr_3$, $CH_2Cl_2$, 0° C.; $H_3PO_4$, R—OH where R is —CH₂CH₂CH₃, —CH(CH₃)₂, —(CH₂)₃CH₃, or —CH₂CH(CH₃)₂, 70-80° C.;

(5) Synthetic route of compound 12

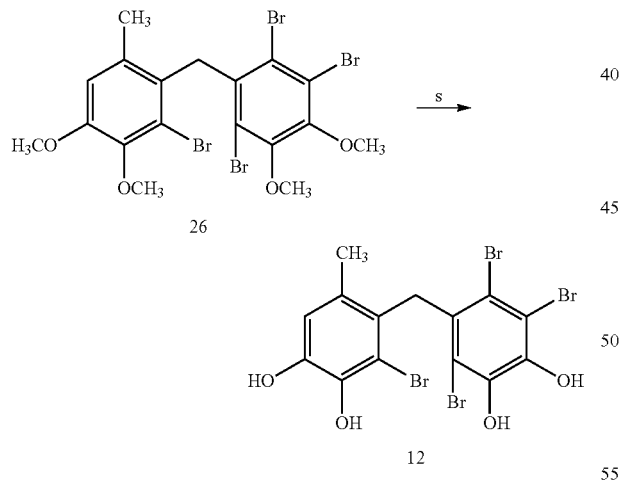

wherein the synthetic route for compound 12 includes Scheme 5 where (n) includes $BBr_3$, $CH_2Cl_2$, 0° C.;

and wherein the method comprises selecting the precursor associated with the synthetic route and performing the series of reactions associated with the selected synthetic route to form the PTP1B inhibitor.

3. The method for preparing the PTP1B inhibitor according to claim 2, wherein Scheme 1 includes:

for (a): under ice bath condition, adding bromine dropwise to a solution of vanilline in MeOH within 1-2 hours, warming the mixture to room temperature and stirring for a further 0.5-1 h and then cooling to 0° C. with added ice water within 20-30 min, and obtaining 5-Br-vanillin;

for (b): at room temperature, adding $CH_3I$ dropwise to a suspension of 5-Br-vanillin and $K_2CO_3$ in DMF, after stirring for 24 h, adding brine to quench the reaction, extracting the mixture with tent-butyl methyl ether forming an organic layer, which is washed and dried to give 5-bromo-veratraldehyde;

for (c): at room temperature, adding hydrazine hydrate to a solution of 5-bromo-veratraldehyde in diglycol, adding KOH and heating the mixture to 110-120° C. to form 5-bromo-3,4-dimethoxy-methylbenzene;.

for (d): at room temperature , adding bromine and iron powder as a catalyst dropwise to a solution of 3-bromo-4,5-dimethoxybenzaldehyde, heating the mixture to 60-70° C. and stirring for 4-6 hours forming 5,6-dibromo-veratraldehyde;

for (e): at 90° C., adding $KMnO_4$ to a solution of $NaHCO_3$ and 5,6-dibromo-veratraldehyde in water, heating the mixture to form 5,6-dibromo-veratric acid; and for (f): under ice bath condition, mixing 5,6-dibromo-veratric acid with 5-bromo-3,4-dimethoxy-methylbenzene to form (2'-bromo-3',4'-dimethoxy-6'-methylphenyl)-(2,3-dibromo-4,5-dimethoxyphenyl)-methanone;

for (g): dissolving (2'-bromo-3',4'-dimethoxy-6'-methylphenyl)-(2,3-dibromo-4,5-dimethoxyphenyl)-methanone and catalyst in $CCl_4$, adding NBS to the solution under hv condition with stirring to obtain (2'-bromo-6'-(dibromomethyl)-3',4'-dimethoxyphenyl)-(2,3-dibromo-4,5-dimethoxyphenyl)-methanone.

4. The method for preparing the PTP1B inhibitor according to claim 2, wherein Scheme 2 includes:

for (h): under ice bath condition, adding $NaBH_4$ to a stirred solution of 5,6-dibromo-veratraldehyde in MeOH, acidifing to a pH of 5-6, evaporating the MeOH to obtain a residue which is extracted to from an organic layer, and dried to obtain 5,6-dibromo-3,4-dimethoxy-phenyl-methanol;

for (i): under ice bath condition, adding $AlCl_3$ to a stirred solution of 5-bromo-3,4-dimethoxy-methylbenzene and 5,6-dibromo-3,4-dimethoxy-phenyl-methanol in $CH_2Cl_2$, obtaining 2,3-dibromo-1-(2'-bromo-3',4'-dimethoxy-6'-methylbenzyl)-4,5-dimethoxy benzene;

for (j): under hv condition, adding NBS to a solution of AIBN or BPO and 2,3-dibromo-1-(2'-bromo-3',4'-dimethoxy-6'-methylbenzyl)-4,5-dimethoxy benzene and in $CCl_4$, removing the solvent to give white solid, dissolving the white solid in a mixture of dixoane and $H_2O$, heating the mixture to 90-100° C., adding $CHCl_3$ and $H_2O$ and then collecting an organic layer, concentrating in vacuo to obtain (3-bromo-2-(2',3'-dibromo-4', 5'-dimethoxybenzyl)-4,5-dimethoxyphenyl)-methanol;

for (k): under 0° C. condition, adding dropwise $BBr_3$ dichloromethane solution to a solution of (3-bromo-2-(2',3'-dibromo-4',5'-dimethoxybenzyl)-4,5-dimethoxyphenyl)-methanol in $CH_2Cl_2$, pouring the mixture into ice-cold water, extracting with EtOAc and collecting an organic layer, and concentrating in vacuo to obtain a residue, dissolving the residue was in iso-propanol, isobutanol and sec-butyl alcohol, respectively to obtain the desired R component, refluxing for 1-2 hours and removing the solvent vacuo to obtain 3,4-dibromo-5-(2-bromo-3,4-dihydroxy-6-(isopropoxymethyl)benzyl) benzene-1,2-diol, 3,4-dibromo-5-(2-bromo-3,4-dihydroxy-6-(isobutoxymethyl)benzyl)benzene-1,2-diol, or 3,4-dibromo-5-(2-bromo-6-(sec-butoxymethyl)-3,4-dihydroxybenzyl)benzene-1,2-diol, based on the alcohol selected.

5. The method for preparing the PTP1B inhibitor according to claim 2, wherein Scheme 3 includes:
   for (l): under ice bath condition, adding AlCl₃ to a solution of veratrole and (3-bromo-2-(2',3'-dibromo-4',5'-dimethoxybenzyl)-4,5-dimethoxyphenyl)-methanol in CH₂Cl₂ with stirring, pouring the mixture into ice-water, washing the organic phase, drying and concentrating in vacuo to obtain 2,3-dibromo-1-(2'-bromo-6'-(3'',4''-dimethoxybenzyl)-3',4'-dimethoxybenzyl)-4,5-dimethoxybenzene; and
   for (m): at room temperature, adding bromine dropwise to a solution of 2,3-dibromo-1-(2'-bromo-6'-(3'',4''-dimethoxybenzyl)-3',4'-dimethoxybenzyl)-4,5-dimethoxybenzene in CH₂Cl₂, evaporating the solvent to form a residue which is dissolved in CHCl₃, washing the organic phase and concentrating in vacuo to obtain 2,3-dibromo-1-(2'-bromo-6'-(2''-bromo-4'',5''-dimethoxybenzyl)-3',4'-dimethoxybenzyl)-4,5-dimethoxybenzene.

6. The method for preparing the PTP1B inhibitor according to claim 2, wherein Scheme 4 includes:
   for (n): under 0° C. condition, adding N-bromosuccinimide to a solution of 5-bromo-veratraldehyde in cond. H₂SO₄, pouring the mixture into ice-cold water, extracting with CHCl₃ to form an organic layer, washing the organic layer and concentrating in vacuo to obtain 2,3,6-tribromo-4,5-dimethoxy-benzaldehyde;
   for (o): under ice bath condition, adding NaBH₄ to a stirred solution of 2,3,6-tribromo-4,5-dimethoxy-benzaldehyde in MeOH, acidifying to a pH of 5-6, evaporating to form a residue which is extracted with CH₂Cl₂ to form an organic layer, concentrating the organic layer in vacuo to obtain 2,3,6-tribromo-4,5-dimethoxy-phenyl-methanol;
   for (p): dissolving 5-bromo-3,4-dimethoxy-methylbenzene and 2,3,6-tribromo-4,5-dimethoxy-phenyl-methanol in CH₂Cl₂, adding AlCl₃, washing the organic layer, and concentrating the organic layer in vacuo to obtain 1,2,4-tribromo-3-(2'-bromo-3',4'-dimethoxy-6'-methylbenzyl)-5,6-dimethoxybenzene;
   for (q): under hv condition, adding NBS to a solution of AIBN or BPO and 1,2,4-tribromo-3-(2'-bromo-3',4'-dimethoxy-6'-methylbenzyl)-5,6-dimethoxybenzene and in CCl₄, removing CCl₄ in vacuo to form a residue, purifying the residue to obtain a white solid, dissolving the white solid in a mixture of dixoane and H₂O, heating the mixture to 90-100° C., adding the mixture to a volume of CHCl₃ and H₂O, collecting the organic layer and concentrating in vacuo to obtain (3-bromo-4,5-dimethoxyphenyl-2-(2',3',6'-tribromo-4',5'-dimethoxybenzyl)phenyl)-methanol;
   for (r): under 0° C. condition, adding dropwise BBr₃ dichloromethane solution to a solution of (3-bromo-4,5-dimethoxyphenyl-2-(2',3',6'-tribromo-4',5'-dimethoxybenzyl)phenyl)-methanol in CH₂Cl₂, stirring the reaction mixture at room temperature, pouring the mixture in ice-cold water and extracting with EtOAc to form an organic layer, which is collected, and concentrated in vacuo to obtain a residue, dissolving the residue in n-propanol, iso-propanol, n-butyl alcohol and isobutanol, depending on the desired R group, respectively, refluxing for 1-2 h, removing the solvent in vacuo. and obtaining 3,4,6-tribromo-5-(2-bromo-3,4-dihydroxy-6-(propoxymethyl)benzyl)benzene-1,2-diol, 3,4,6-tribromo-5-(2-bromo-3,4-dihydroxy-6-(isopropoxymethyl)benzyl)benzene-1,2-diol, 3,4,6-tribromo-5-(2-bromo-6-(butoxy methyl)-3,4-dihydroxybenzyl)benzene-1,2-diol, or 3,4,6-tribromo-5-(2-bromo-3,4-dihydroxy-6-(isobutoxymethyl)benzyl)benzene-1,2-diol, depending on the alcohol used.

7. The method for preparing the PTP1B inhibitor according to claim 2, wherein Scheme 5 includes:
   for (s): under 0° C. condition, adding dropwise BBr₃ dichloromethane solution to a solution of 1,2,4-tribromo-3-(2'-bromo-3',4'-dimethoxy-6'-methylbenzyl)-5,6-dimethoxybenzene in CH₂Cl₂, stirring the reaction mixture, pouring the mixture into ice-cold water and extracting and then collecting the organic lay, and concentrating in vacuo to obtain 3,4,6-tribromo-5-(2'-bromo-3',4'-dihydroxy-6'-methylbenzyl)benzene-1,2-diol.

8. A method for treating type 2 diabetes mellitus comprising administering to a subject the PTP1B inhibitors according to claim 1.

9. The PTP1B inhibitor of claim 1 selected from the group consisting of 3,4,6-tribromo-5-(2-bromo-3,4-dihydroxy-6-(propoxymethyl)benzyl)benzene-1,2-diol (6), 3,4,6-tribromo-5-(2-bromo-3,4-dihydroxy-6-(isopropoxymethyl) benzyl)benzene-1,2-diol (8), 3,4,6-tribromo-5-(2-bromo-6-(butoxymethyl)-3,4-dihydroxybenzyl)benzene-1,2-diol (9), 3,4,6-tribromo-5-(2-bromo-3,4-dihydroxy-6-(isobutoxymethyl)benzyl)benzene-1,2-diol (10), 3,4,6-tribromo-5-(2-bromo-3,4-dihydroxy-6-(secbutoxymethyl)benzyl)benzene-1,2-diol (11), and 3,4,6-tribromo-5-(2-bromo-3,4-dihydroxy-6-methyl benzyl)benzene-1,2-diol (12).

10. An agent of PTP1B inhibitor, which contains one or more of the followed four compounds as active components, and the structures of the four compounds are as follows:

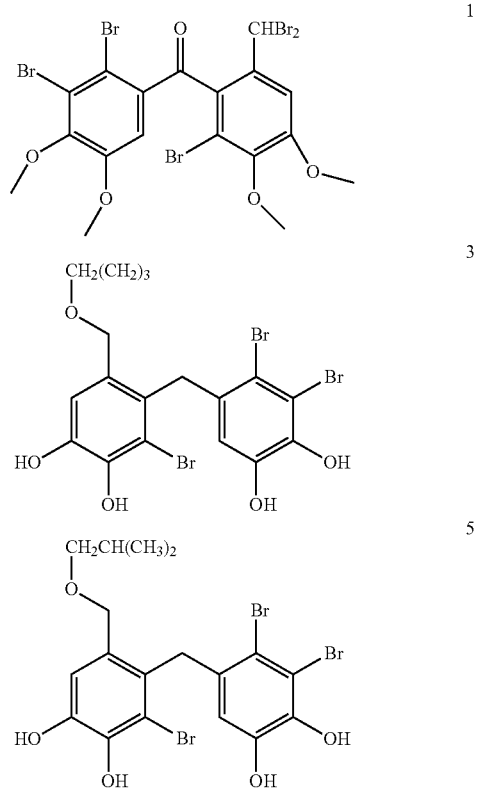

-continued
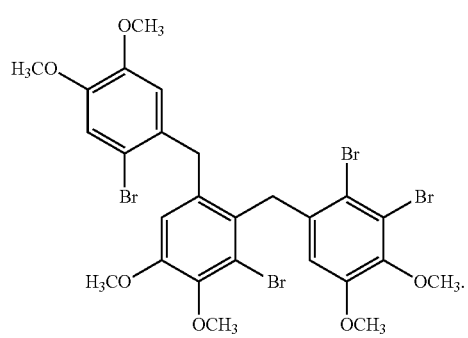
6
Their chemical names are: (2'-bromo-6'-(dibromomethyl)-3',4'-dimethyoxypheny)-2,3-dibromo-4,5-dimethoxyphenyl)-methanone (1); 3,4-dibromo-5-[2'-bromo-3',4'-dihydroxy-6'-(isopropoxymethyl)-benzyl]-benzene-1,2-diol (3), 3,4-dibromo-5-[2'-bromo-3',4'-dihydroxy-6'-(isobutoxymethyl)-benzyl]-benzene-1,2-diol (5); 2,3-dibromo-1-[2'-bromo-6'-(2''-bromo-4'',5''-dimethoxybenzyl)-3',4'-dimethoxybenzyl]-4,5-dimethoxybenzene (6).
* * * * *